US012322185B2

(12) United States Patent
Ranasinghe et al.

(10) Patent No.: US 12,322,185 B2
(45) Date of Patent: Jun. 3, 2025

(54) SYSTEM AND METHOD FOR MONITORING CLINICAL ACTIVITIES

(71) Applicant: Masimo Corporation, Irvine, CA (US)

(72) Inventors: Nadeesha O. Ranasinghe, Laguna Niguel, CA (US); Ammar Al-Ali, San Juan Capistrano, CA (US); Massi Joe E. Kiani, Laguna Niguel, CA (US); Mohammad Usman, Mission Viejo, CA (US); Bowen Zhao, Irvine, CA (US); Pierre de Malliard, Laguna Beach, CA (US); Peter Sunghwan Min, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/514,662

(22) Filed: Nov. 20, 2023

(65) Prior Publication Data
US 2024/0085545 A1 Mar. 14, 2024

Related U.S. Application Data

(63) Continuation of application No. 17/174,965, filed on Feb. 12, 2021, now Pat. No. 11,879,960.
(Continued)

(51) Int. Cl.
G01S 11/12 (2006.01)
G06N 3/044 (2023.01)
G06V 10/764 (2022.01)
G06V 10/82 (2022.01)
G06V 20/52 (2022.01)
(Continued)

(52) U.S. Cl.
CPC .............. *G06V 20/52* (2022.01); *G01S 11/12* (2013.01); *G06N 3/044* (2023.01); *G06V 10/764* (2022.01); *G06V 10/82* (2022.01); *G06V 40/10* (2022.01); *G06V 40/103* (2022.01); *G06V 40/20* (2022.01);
(Continued)

(58) Field of Classification Search
CPC .... G08B 21/245; G06N 3/0445; G06N 7/005; G06N 3/0454; G06V 10/40; G06V 20/52; G06V 40/10; G06V 40/20; G06V 10/82; G06V 10/764; G06V 40/103; H04N 5/247; G01S 11/12
See application file for complete search history.

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

WO WO 2021/163447 8/2021

OTHER PUBLICATIONS

US 2022/0192529 A1, 06/2022, Al-Ali et al. (withdrawn)
(Continued)

Primary Examiner — Adnan Aziz
(74) Attorney, Agent, or Firm — Knobbe, Martens, Olson & Bear, LLP

(57) ABSTRACT

A monitoring system can be configured to monitor activities or actions occurring in clinical settings, such as hospitals. The monitoring system can improve patient safety. The system can use visual and/or other tracking methods. The system can detect and/or identify people in a clinical setting. The system can also track activities of the people, for example, to improve adherence to hygiene protocols.

20 Claims, 24 Drawing Sheets

Related U.S. Application Data

(60) Provisional application No. 63/085,058, filed on Sep. 29, 2020, provisional application No. 63/075,731, filed on Sep. 8, 2020, provisional application No. 62/976,000, filed on Feb. 13, 2020.

(51) Int. Cl.
  *G06V 40/10* (2022.01)
  *G06V 40/20* (2022.01)
  *G08B 21/24* (2006.01)
  *G16H 40/20* (2018.01)
  *G16H 50/80* (2018.01)
  *H04N 23/90* (2023.01)

(52) U.S. Cl.
  CPC .......... *G08B 21/245* (2013.01); *G16H 40/20* (2018.01); *G16H 50/80* (2018.01); *H04N 23/90* (2023.01)

(56) References Cited

U.S. PATENT DOCUMENTS

| | | | |
|---|---|---|---|
| 5,319,355 A | 6/1994 | Russek | |
| 5,337,744 A | 8/1994 | Branigan | |
| 5,341,805 A | 8/1994 | Stavridi et al. | |
| 5,377,676 A | 1/1995 | Vari et al. | |
| 5,431,170 A | 7/1995 | Mathews | |
| 5,436,499 A | 7/1995 | Namavar et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,812,059 A * | 9/1998 | Shaw ............... | G08B 21/245 340/539.1 |
| 5,890,929 A | 4/1999 | Mills et al. | |
| 5,919,134 A | 7/1999 | Diab | |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,232,609 B1 | 5/2001 | Snyder et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,360,114 B1 | 3/2002 | Diab et al. | |
| 6,368,283 B1 | 4/2002 | Xu et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,658,276 B2 | 12/2003 | Kiani et al. | |
| 6,661,161 B1 | 12/2003 | Lanzo et al. | |
| 6,697,656 B1 | 2/2004 | Al-Ali | |
| 6,697,658 B2 | 2/2004 | Al-Ali | |
| RE38,476 E | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| 6,920,345 B2 | 7/2005 | Al-Ali et al. | |
| 6,934,570 B2 | 8/2005 | Kiani et al. | |
| 6,943,348 B1 | 9/2005 | Coffin, IV | |
| 6,956,649 B2 | 10/2005 | Acosta et al. | |
| 6,961,598 B2 | 11/2005 | Diab | |
| 6,970,792 B1 | 11/2005 | Diab | |
| 6,975,231 B2 * | 12/2005 | Lane ................... | G08B 21/245 340/603 |
| 6,985,764 B2 | 1/2006 | Mason et al. | |
| 6,990,364 B2 | 1/2006 | Ruchti et al. | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,225,006 B2 | 5/2007 | Al-Ali et al. | |
| RE39,672 E | 6/2007 | Shehada et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,356,365 B2 | 4/2008 | Schurman | |
| 7,371,981 B2 | 5/2008 | Abdul-Hafiz | |
| 7,373,193 B2 | 5/2008 | Al-Ali et al. | |
| 7,377,794 B2 | 5/2008 | Al-Ali et al. | |
| 7,395,158 B2 | 7/2008 | Monfre et al. | |
| 7,415,297 B2 | 8/2008 | Al-Ali et al. | |
| 7,438,683 B2 | 10/2008 | Al-Ali et al. | |
| 7,483,729 B2 | 1/2009 | Al-Ali et al. | |

(56) References Cited

U.S. PATENT DOCUMENTS

| | | |
|---|---|---|
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| 8,090,155 B2 * | 1/2012 | Lacey ............... G08B 21/245 382/209 |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,235,977 B2 | 1/2016 | Deutsch |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |

(56) References Cited

U.S. PATENT DOCUMENTS

| | | |
|---|---|---|
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,147,191 B1 | 12/2018 | Ribeiro et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,485,454 B2 | 11/2019 | Tas et al. |
| 10,505,311 B2 | 12/2019 | Al-Ali et al. |
| 10,524,738 B2 | 1/2020 | Olsen |
| 10,529,219 B2 | 1/2020 | Herdt et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,645,346 B2 | 5/2020 | Clark |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| 10,754,924 B2 * | 8/2020 | Katz ..................... G16H 70/20 |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |

(56) References Cited

U.S. PATENT DOCUMENTS

| | | |
|---|---|---|
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| D1,041,511 S | 9/2024 | Indorf et al. |
| 12,076,159 B2 | 9/2024 | Belur Nagaraj et al. |
| D1,044,828 S | 10/2024 | Chandran et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0091458 A1* | 4/2009 | Deutsch ............... G16H 40/20 705/2 |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0328443 A1* | 12/2010 | Lynam ............... G08B 21/245 348/E7.085 |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0075464 A1 | 3/2012 | Derenne et al. |
| 2012/0123231 A1 | 5/2012 | O'Reilly |
| 2012/0154582 A1* | 6/2012 | Johnson ............... G06Q 10/00 340/521 |
| 2012/0165629 A1 | 6/2012 | Merritt et al. |
| 2012/0209084 A1 | 8/2012 | Olsen et al. |
| 2012/0212582 A1 | 8/2012 | Deutsch |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0109442 A1* | 4/2015 | Derenne ............... H04N 7/185 348/143 |
| 2015/0302769 A1* | 10/2015 | Johnson ............. G09B 19/0076 434/308 |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0068179 A1 | 3/2018 | Derenne et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0310823 A1 | 11/2018 | Al-Ali et al. |
| 2019/0117070 A1 | 4/2019 | Muhsin et al. |
| 2019/0239787 A1 | 8/2019 | Pauley et al. |
| 2019/0253668 A1 | 8/2019 | Kusens |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |

(56) References Cited

U.S. PATENT DOCUMENTS

| | | |
|---|---|---|
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0349346 A1 | 11/2020 | Gefen et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2023/0401865 A1 | 12/2023 | Ranasinghe et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |

OTHER PUBLICATIONS

US 2024/0016391 A1, 01/2024, Lapotko et al. (withdrawn)

International Search Report and Written Opinion in PCT Application No. PCT/US2021/017812, dated Jul. 26, 2021 in 22 pages.

Intille et al., "Real-Time Closed-World Tracking", Computer Vision and Pattern Recognition, 1997, Proceedings, 1997 IEEE Computer Society Conference on San Juan, Puerto Rico, Jun. 17-19, 1997, pp. 697-703.

Krumm et al., "Multi-Camera Multi-Person Tracking for Easy Living", IEEE Workshop on Visual Surveillance Proceedings, Jul. 1, 2000, pp. 3-10.

* cited by examiner

SYSTEM AND METHOD FOR MONITORING CLINICAL ACTIVITIES

INCORPORATION BY REFERENCE TO ANY PRIORITY APPLICATIONS

The present application is a continuation of U.S. application Ser. No. 17/174,965, filed Feb. 12, 2021, which claims priority benefit under 35 U.S.C. § 119(e) to U.S. Provisional Application No. 62/976,000, filed Feb. 13, 2020, U.S. Provisional Application No. 63/075,731, filed Sep. 8, 2020, and U.S. Provisional Application No. 63/085,058, filed Sep. 29, 2020, the entirety of each of which is hereby incorporated by reference. Any and all applications for which a foreign or domestic priority claim is identified in the Application Data Sheet as filed with the present application are hereby incorporated by reference under 37 CFR 1.57.

FIELD

The present disclosure relates to monitoring of clinical activities.

BACKGROUND

Patient safety is of great importance in a clinical setting, such as in a hospital. Monitoring of the people and/or objects at the clinical setting, and/or whether hygiene protocols are being observed, can improve patient safety.

SUMMARY

The present disclosure provides a system for tracking, on a local network, movements of people in an enclosed room with an entrance/exit. The system may comprise a camera configured to capture image data from a viewpoint in the room and a hardware processor in physical proximity to the camera. The hardware processor may be configured to detect each person in an image frame from the image data, extract coordinates of each detected person relative to the image frame and update tracks monitored by the hardware processor based on the coordinates of each detected person. A new track may be assigned to a person detected within a predetermined distance from the entrance/exit and not having been assigned a track in a previous image frame from the image data.

In some configurations, in response to a person detected within the predetermined distance from the entrance/exit and having been assigned a track in the previous image frame from the image data, the hardware processor may be configured to delete the track.

In some configurations, in response to a person detected away from the entrance/exit by the predetermined distance and having been assigned a track in the previous image frame from the image data, the hardware processor may be configured to confirm the track.

In some configurations, the enclosed room may be a clinical room and the hardware processor further may be configured to assign a contaminated status to any person who is assigned a new track.

In some configurations, the hardware processor may be further configured to change the contaminated status of a person upon detecting the person performing a hand hygiene activity.

In some configurations, the system may further comprise a second camera which may be configured to capture image data from a second viewpoint in the room and the system may comprise a second hardware processor in physical proximity to the second camera. The second viewpoint may include a view of a hand hygiene area and the second processor may be configured to detect the hand hygiene activity.

In some configurations, the hardware processor may be configured to output an alert to a display device in the clinical room in response to detecting a track of a contaminated person entering a patient zone.

In some configurations, the processor may be configured to determine that a track in a previous image frame belongs to the same person detected in the image frame by performing an intersection over union calculation of coordinates of the track in the previous image frame and the coordinates of the person detected in the image frame.

In some configurations, the system may comprise a plurality of cameras and a plurality of hardware processors, each of the plurality of cameras may be in physical proximity and associated with one of the plurality of hardware processors.

In some configurations, the plurality of hardware processors may be configured to resolve occlusion based at least in part on a number of tracks detected in an image frame from image data of their respective associated cameras.

The present disclosure provides a system for monitoring hand hygiene compliance on a local network in an enclosed room with an entrance/exit. The system may comprise a camera configured to capture image data from a viewpoint in the room and a hardware processor in physical proximity to the camera. The hardware processor may be configured to detect each person in an image frame from the image data and extract features related to activities of each detected person from a plurality of image frames in sequence and analyze the extracted features to determine whether a hand hygiene activity has been performed by each detected person.

In some configurations, the hardware processor may be configured to extract features related to activities of each detected person from each image frame of the plurality of image frames in sequence using a convolutional neural network.

In some configurations, the hardware processor may be configured to analyze the extracted features using a recurrent neural network.

In some configurations, the recurrent neural network may be configured to analyze the extracted features to determine whether a step of the hand hygiene activity has been performed. The hand hygiene activity may comprise a plurality of steps.

In some configurations, the hardware processor may be configured to output a binary determination of whether a hand hygiene activity has been performed by each detected person.

In some configurations, the hardware processor may be configured to output a score of a detected hand hygiene activity.

The present disclosure provides a system for monitoring of hand hygiene compliance on a local network in a clinical room. The system may comprise a first camera configured to capture first image data from a first viewpoint in the clinical room and a first hardware processor in physical proximity to the first camera. The first processor may be configured to detect a person in an image frame from the first image data and assign a boundary box to the person. The first processor may be further configured to track movement of the boundary box in subsequent image frames from the first image data. The system may comprise a second camera which may be configured to capture second image data from a second viewpoint in the clinical room and a second hardware processor in physical proximity to the second camera. The second processor may be configured to detect a hand hygiene activity from the second image data. The first and second processors may be in electrical communication with each other. The first or second processor may be configured to determine whether the detected hand hygiene activity was performed by the person to whom the boundary box is assigned. The first processor and/or the second processor may be in electrical communication with a display device in the clinical room. The first and/or second processors may configured to output an alert to the display device in the clinical room in response to the boundary box entering a patient zone without the second processor detecting a hand hygiene activity by the person to whom the boundary box is assigned.

In some configurations, the first processor may be configured to output an alert directly to the display device in the clinical room.

In some configurations, the first and second viewpoints may be fixed.

In some configurations, the first camera may face an entrance of the clinical setting.

In some configurations, the second camera may face a hand hygiene station.

In some configurations, the second camera may face downward at the hand hygiene station.

In some configurations, the hand hygiene station may comprise a sink and/or a hand sanitizer dispenser.

In some configurations, the second processor may be configured to detect a handwashing activity at the sink.

In some configurations, the second processor may be configured to detect a hand sanitizing activity at the sink.

In some configurations, the system may comprise a third camera. The third camera may be configured to capture third image data from a third viewpoint in the clinical room.

In some configurations, the first processor may be configured to assign a contaminated status to any person upon first detection of said person.

In some configurations, the first or second processor may be configured to change a contaminated status of the person to a clean status upon detection of the person having performed the hand hygiene activity.

In some configurations, the first and/or second processors may be configured to receive configuration information of the clinical room from a server upon initiation of the system.

In some configurations, the system may comprise one or more display devices. The configuration information may comprise one or more of display device locations, camera locations, entrance location, hand hygiene station location, and/or patient bed location.

In some configurations, the first and/or second processor may be configured to determine, based at least in part on the configuration information, a nearest display device to the person who enters the patient zone without the second processor detecting a hand hygiene activity by the person.

In some configurations, no image data from the first or second cameras may be transmitted to the server.

In some configurations, no image data from the first or second cameras may be transmitted to the display device.

In some configurations, no image data from the first or second cameras may be stored or recorded anywhere.

In some configurations, the first and/or second processors may not perform facial recognition or ID tag identification of a person detected in an image frame from the first and/or second image data respectively.

In some configurations, the first and/or second processors may be configured to perform facial recognition of a person detected in an image frame from the first and/or second image data respectively.

In some configurations, the first and/or second processors may perform ID tag identification of a person detected in an image frame from the first and/or second image data respectively.

In some configurations, the second processor may be configured to detect a hand hygiene activity from the second image data by extracting hand hygiene-related features from image frames of the second image data.

In some configurations, the second processor may be further configured to output whether a hand hygiene activity has been performed based at least in part on the extracted hand hygiene-related features.

In some configurations, the second processor may be further configured to determine whether a hand hygiene protocol has been complied with based at least in part on the extracted hand hygiene-related features.

In some configurations, the second processor may be configured to detect a hand hygiene activity from the second image data using deep learning modules.

The present disclosure provides a system for tracking movements of a person in a clinical room wherein more than one person may be present at the clinical room. The system may comprise a first camera configured to capture first image data from a first viewpoint in the clinical room and a first hardware processor in physical proximity to the first camera. The first processor may be configured to detect each person in an image frame from the first image data and assign a unique boundary box to each person. The first processor may be further configured to track movement of the boundary boxes in subsequent image frames from the first image data. The system may comprise a second camera configured to capture second image data from a second viewpoint in the clinical room and a second hardware processor in physical proximity to the second camera. The second processor may be configured to detect each person in an image frame from the second image data and assign a unique boundary box to each person. The second processor may be further configured to track movement of the boundary boxes in subsequent image frames from the second image data. At least one of the first or second cameras may comprise a depth camera. The first and/or second processor may be configured to detect occlusion of a person in the clinical room by another person or object using depth information from the depth camera.

In some configurations, the first and second viewpoints may be fixed.

In some configurations, the first camera may face an entrance of the clinical room.

In some configurations, the clinical room may consist of a single entrance.

In some configurations, the system may comprise a third camera. The third camera may be configured to capture third image data from a third viewpoint in the clinical room.

In some configurations, the third camera may comprise a depth camera.

In some configurations, the first and second cameras may each comprise a depth camera.

In some configurations, the depth information of the first camera may translate to information in a direction of the second camera that is orthogonal to Z axis of the first camera.

In some configurations, the depth information of the first camera may be orthogonal to depth information of the second camera.

In some configurations, the first and/or second processors may be configured to detect occlusion of a person if the first processor is tracking a different number of boundary boxes than the second processor.

In some configurations, the first and second processors may track movement of each person in the room independently.

In some configurations, the first and/or second processors may not perform facial recognition or ID tag identification of a person detected in an image frame of the first and/or second image data respectively.

In some configurations, the first and/or second processors may perform facial recognition of a person detected in an image frame of the first and/or second image data respectively.

In some configurations, the first and/or second processors may perform ID tag identification of a person detected in an image frame of the first and/or second image data respectively.

The present disclosure provides a system for tracking movements of a person in a clinical room, wherein more than one person may be present at the clinical room. The system may comprise a camera configured to capture image data from a viewpoint in the clinical room. The system may comprise a hardware processor in physical proximity to the camera. The processor may be configured to detect each person in an image frame from the image data and assign a unique boundary box to each person. The processor may be further configured to track movement of the boundary boxes in subsequent image frames from the image data. The processor may assign a first boundary box in a first image frame to a person detected in the first image frame and a second boundary box in a second, subsequent image frame to a person detected in the second, subsequent image frame. The processor may be configured to assign the first and second boundary boxes to the same person in response to the first and second boundary boxes being the closest compared to a distance between the first boundary box and a remainder of boundary boxes in the second, subsequent image frame.

In some configurations, the camera may comprise a color and depth camera.

In some configurations, the processor may be configured to assume a walking or running speed limit of a person detected in the first image frame.

In some configurations, the processor may be configured to assign the first and second boundary boxes to the same person, in response to an overlap between the first and second boundary boxes exceeding a threshold.

In some configurations, the processor may be configured to perform mask detection of a person detected in an image frame of the image data.

In some configurations, the processor may be further configured to perform facial recognition of a person detected in an image frame of the image data if the processor has detected no mask in said image frame.

In some configurations, the processor may be configured to perform ID tag detection of a person detected in an image frame of the image data.

In some configurations, the processor may be further configured to perform ID tag identification of a person detected in an image frame of the image data if the processor has detected an ID tag in said image frame.

In some configurations, the processor may be configured to ignore a head not within a determined proximity to a boundary box.

In some configurations, the processor may be configured to ignore one or more of heads and/or hands that exceed a predetermined size limit.

In some configurations, the processor may be configured to ignore a boundary box that exceeds a predetermined size limit.

In some configurations, the predetermined size limit(s) discussed above may be based, at least in part, on a distance between a detected object and the camera.

In some configurations, the processor may be configured to measure the distance between a detected person and the camera by measuring by the distance between the head of the detected person and the camera.

In some configurations, the processor may be configured to measure the distance between the head of a detected person and the camera by averaging the distance to pixels detected on the head of the detected person.

In some configurations, the processor may be configured to assign a boundary box to a detected person if the person has been detected in a predefined number of consecutive image frames.

In some configurations, the camera may be configured to capture image data at a frame rate of at least 20-30 frames per second.

In some configurations, the processor may be configured to delete a boundary box when the person to whom the boundary box has been assigned has not been detected in a predetermined number of consecutive image frames of the image data.

In some configurations, the processor may be configured to delete a boundary box when the person to whom the boundary box has been assigned is within a predefined proximity to an entrance/exit region of the clinical room.

In some configurations, the processor may be configured to create a boundary box when a person is detected in a predetermined number of consecutive frames within a predetermined proximity to an entrance/exit region of the clinical room.

In some configurations, the processor may be configured to create a boundary box when a person is detected in a predetermined number of consecutive frames anywhere in the clinical room.

In some configurations, the processor may be configured to assign a missing status to a boundary box that is not assigned to a person.

In some configurations, the processor may be configured to assign a boundary box with a missing status to a detected person within a predetermined proximity of said boundary box. The predetermined proximity may be proportionate to the amount of time said boundary box has had a missing status.

The present disclosure provides a system for monitoring activities or actions occurring in a clinical setting that includes a plurality of sensors including a first camera and a second camera in the clinical setting, the first and second cameras being high-resolution cameras and relative positions of the first and second camera being substantially fixed, the plurality of sensors further comprising at least one camera processor in electrical communication with the first and/or second cameras, wherein the first and second cameras can be generally facing a fixed object at different angles, and wherein the at least one camera processor can be in electrical communication with a server that includes a server processor separate from the at least one camera processor, the at least one camera processor configured to process images captured by the first and/or second cameras to output non-image data to the server.

In some configurations, the system can include a third camera coupled to a second camera processor that is in electrical communication with the server to output second non-image data based on images captured by the third camera, wherein the third camera can facing a different fixed object of the clinical setting than the first and second cameras.

In some configurations, the server can be configured to update trackers associated with the first and second cameras based on the non-image data and update trackers associated with the third camera based on the second non-image data.

In some configurations, the server can be configured to update a latest status of a detected person in a database of the server based on the updated trackers.

In some configurations, the non-image data can include boundary box coordinates, tag identifier information, extracted facial features, activity features, camera identifier information, unique ID for each person, frame number of the images, or any combinations thereof.

In some configurations, the first, second, and/or third cameras can be configured to prioritize detection of the unique ID for each person.

In some configurations, the unique ID can be detected from an identification tag worn by a detected person.

In some configurations, the identification tag can include a color-coded unique ID tag.

In some configurations, the identification tag can include a Bluetooth Low Energy unique ID tag.

In some configurations, the fixed object can be a hospital bed.

In some configurations, the first and second cameras can be at opposite sides of the hospital bed.

In some configurations, the different fixed object can include a handwashing station.

In some configurations, the system can include a fourth camera facing the handwashing station, the fourth camera in electrical communication with the second camera processor.

In some configurations, the first and/or second cameras can be configured to detect whether a detected person is within a contaminated zone.

In some configurations, the server can be configured to output an alarm in response to detecting the detected person returning to the same contaminated zone or entering a different contaminated zone without having washed hands.

In some configurations, the system can include a plurality of displays, the server can be configured to output the alarm to one of the plurality of displays that is nearest to the detected person.

In some configurations, the plurality of displays can include displays of a plurality of patient-monitoring systems.

In some configurations, the server can be configured to change the detected person's hygiene status from contaminated to clean in response to the detected person completing a handwashing action at the handwashing station after leaving the contaminated zone.

In some configurations, the plurality of sensors can include at least one microphone.

The present disclosure provides a visual system for identifying people and/or objections. The system can include a multi-colored marker comprising a unique pattern of colors, wherein adjacent colors of the pattern are different, wherein the marker can be configured to be captured in an image acquired by a high-resolution camera, the camera comprising a processor configured to: process an image, identify the unique pattern of colors, and output a unique identification number based on the unique pattern of colors.

In some configurations, the marker can include a border enclosing the unique pattern of colors.

In some configurations, the unique sequence of pattern can include a sequence of colors preceded by a header color.

In some configurations, the processor can be configured to reverse the identified sequence upon detecting the header color on a right hand side of the sequence.

In some configurations, the colors can include one or more colors from the CMY color model.

In some configurations, the processor can be configured to output the unique identification number upon determining that the number of colors conform with a parity rule.

In some configurations, the processor can be configured to weigh a number of each color based on a position of the color in the unique pattern.

In some configurations, the processor can further include a people tracking module configured to detect and/or track people.

The present disclosure can provide a system for monitoring activities or actions occurring in a clinical setting. The system can include a plurality of sensors including a first camera and a second camera in the clinical setting, the first and second cameras being high-resolution cameras and relative positions of the first and second camera being substantially fixed, the first camera including a first processor configured to: using a face recognition module, process an image acquired by the first camera, the image comprising a person and/or an object at the clinical setting; and output an identification and/or tracking of the person and/or object based on the processing; the second camera including a second processor configured to: process an image acquired by the second camera, the image comprising the person and/or the object; and output identification and/or tracking of a tag located on the person and/or object, wherein the first processor, the second processor, or a server of the system is configured to combine the identification and/or tracking by the first processor with the identification and/or tracking by the second processor to output a determination of an identity and/or location of the person and/or object.

In some configurations, the person can include a healthcare provider, a patient, and/or a visitor.

In some configurations, the object can include a glove, a gown, a mask, or any combinations thereof.

In some configurations, the second processor can be configured to process an image of a unique pattern of colors on the tag.

In some configurations, adjacent colors in the pattern can be different.

In some configurations, the tag can include a Bluetooth or BLE tag, or an RFID tag.

In some configurations, the face recognition module can be configured to extract facial features and/or appearance features.

In some configurations, the first and/or second processors can be configured to output an alert upon detecting an unauthorized person.

In some configurations, the first and/or second processors can be configured to detect predetermined motions of the person.

In some configurations, the predetermined motions can include a handwashing action and/or a patient-touching action.

In some configurations, the first or second processor can be configured to output an alert upon detecting non-compliant motions.

In some configurations, the first processor can be configured to output a boundary box associated with the person.

In some configurations, the second processor can be configured to output a boundary box associated with the tag.

In some configurations, the first and/or second processors can be configured to transmit information associated with the boundary box to the server.

In some configurations, the first and/or second processors may not send the first and second images to the central server.

In some configurations, the first and second cameras can face generally the same direction.

In some configurations, one of the first or second cameras can be located generally behind the other one of the first or second cameras.

The present disclosure provides a system for monitoring activities or actions occurring in a clinical setting. The system can include a plurality of sensors including a first camera and a second camera in the clinical setting, the first and second cameras being high-resolution cameras and relative positions of the first and second camera being substantially fixed, the first camera including a first processor configured to: process a first image acquired by the first camera, the first image including a first person and a second person at the clinical setting; and determine a first virtual boundary around the first person and a second virtual boundary around the second person based on the processing; the second camera including a second processor configured to: process a second image acquired by the second camera, the second image including the first person and the second person; and output a third virtual boundary around the first person and a fourth virtual boundary around the second person based on the processing, wherein the first processor or a processor at a server of the system can be configured to match the first virtual boundary with the third virtual boundary, and/or the second virtual boundary with the fourth virtual boundary based at least in part on epipolar geometry.

In some configurations, the first and/or second processors can be configured to identify the first person and the second person using a face recognition module and/or by detecting identification tags worn by the first person and the second person.

In some configurations, the first processor or the processor at the server can be configured to combine identification by the first and second processors to output a determination of identities of the first person and second person.

In some configurations, the first person and/or second person can include a healthcare provider, a patient, and/or a visitor.

In some configurations, the first processor or the processor at the server of the system can be configured to project lines from corners of the first virtual boundary to the second image.

In some configurations, the second processor or the processor at the server of the system can be configured to determine a zone in the second image covered by the projected lines.

In some configurations, the second processor or the processor at the server of the system can be configured to determine which of the third and fourth virtual boundaries fit better within the zone.

In some configurations, the first processor or the processor at the server can be configured to compare the first and second virtual boundaries with a zone in the first image covered by lined projected by the second processor.

In some configurations, the first, second, third, and/or fourth virtual boundaries can include rectangles.

In some configurations, the first and/or second processors can be configured to transmit information associated with the first, second, third, and/or fourth virtual boundaries to the processor at the server.

In some configurations, the first and/or second processors may not send the first and second images to the processor at the server.

For purposes of summarization, certain aspects, advantages and novel features are described herein. Of course, it is to be understood that not necessarily all such aspects, advantages or features need to be present in any particular embodiment.

BRIEF DESCRIPTION OF THE DRAWINGS

The drawings and the associated descriptions are provided to illustrate embodiments of the disclosure and not to limit the scope of the claims.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Hand hygiene contributes significantly to keeping patients safe. However, the average hand hygiene compliance is currently less than 40%. In the U.S., about 1.7 million healthcare-associated infections (HAI) occur each year, causing about 99,000 fatalities. About 9.4% of the total inpatient costs are HAI-related, with more than ⅔ of the HAIs affecting people with Medicare or Medicaid. If admitted to a hospital in the U.S., a patient has a 5% chance of contracting an HAI. A patient's length of stay in the hospital can be increased by about 17.6 days if the patient contacts an HAI during the hospital stay. Increasing hand hygiene compliance can reduce the HAI occurrences and thereby improve quality of patient care, while reducing healthcare costs.

Example Clinical Activity Tracking Systems

Figure 9A:
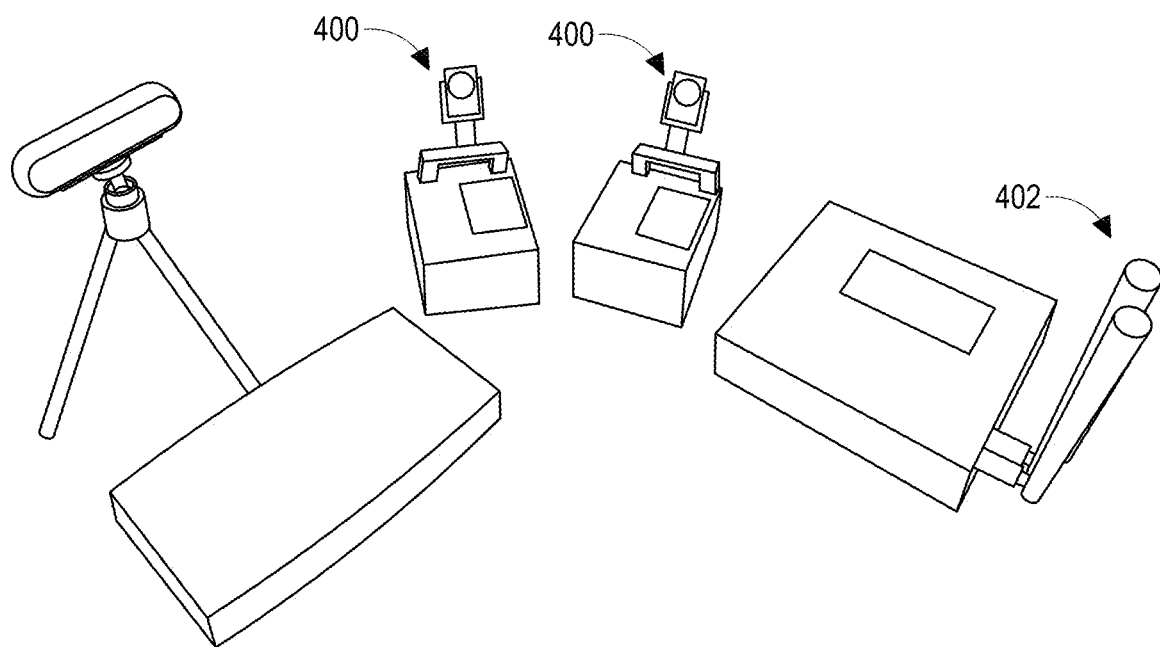
FIG. 9A illustrates example video and/or audio monitoring equipment of an example clinical activities monitoring system.

The present disclosure provides example clinical activities monitoring systems that improve patient safety, such as shown in FIGS. 1A-1C and 2A-2C. The system can include multiple sensor modalities to monitor a variety of activities, and may mitigate errors from a single modality. The monitoring can occur substantially real-time. The sensor modalities can include, but are not limited to, video monitoring, audio monitoring, and/or tagging and tracking of people and/or objects. FIG. 9A illustrate example embodiments of cameras 400 and/or microphones 402, which can be part of the sensor modalities in the system. The sensor modalities can each include its own processing unit to avoid having to send raw data to a central server. Video monitoring may facilitate monitoring of hand hygiene, patient fall detection and/or prevention, patient-touching actions, and likewise. Audio monitoring may facilitate monitoring of calls for help, patient breathing, and likewise. Tagging and tracking can facilitate access control, motion-based activities, and the like. The monitoring of motion-based activities can be achieved optionally by combining video monitoring and tagging and tracking. Access control can also be achieved optionally by combining video monitoring and tagging and tracking.

Figure 1A:
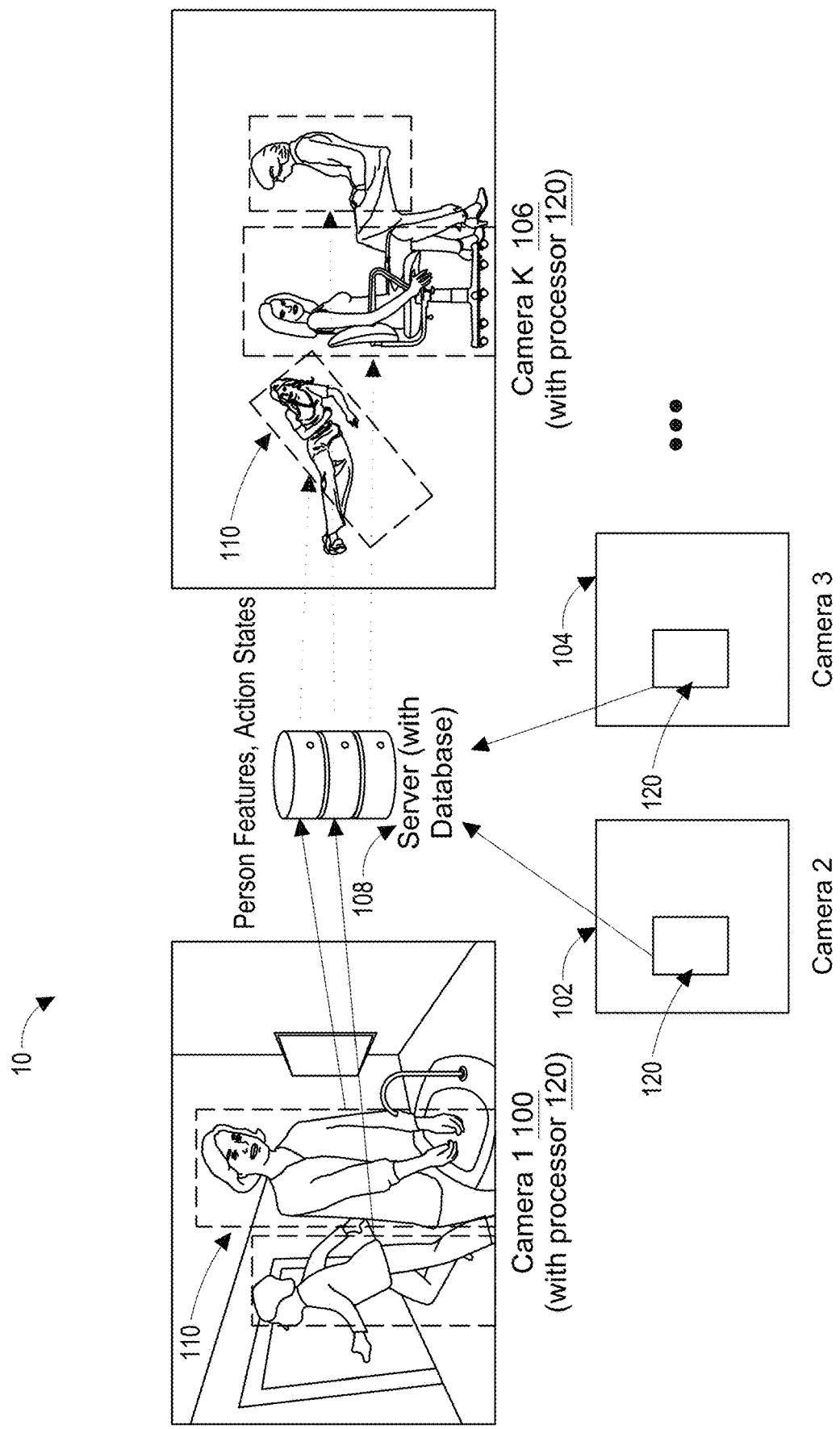
FIG. 1A is a schematic system diagram illustrating an example clinical activities monitoring system.

As shown in FIG. 1A, the system 10 can include a plurality of cameras (for example, Camera 1 100, Camera 2 102, Camera 3 104, . . . , up to Camera K 106). The cameras can be high-resolution cameras, for example, having a resolution as high as 4K (or 8 MP), or more. Non-limiting camera models can include, for example, the See3CAM_130 camera model from the e-con Systems, the Intel Real Sense Depth Camera D415, or likewise.

In the present disclosure, processing of the raw images captured by the cameras can be performed solely by the processing power of the combination of the processors 120 on the cameras. Processed data from the images can be sent from the cameras to the central server 108, which can include trackers (see FIG. 1B) that are associated with individual cameras and updated based on the received processed data and a database (see FIG. 1B) of the latest monitored clinical activities.

The processed data may not include the identified person's face and/or body. As shown in FIG. 1A, the processed data can include information associated with an outline or virtual box (also referred to as a "boundary box") 110 of the person, for example, the coordinates of the box 110. The outline can be a generally rectangular box or of a different shape. Details of the components for generating the outlines will be described below. In this disclosure, the boundary boxes, numbers, and/or names illustrated as being displayed in a camera image are used to illustrate the functions of the clinical activity monitoring system. Frames that include raw images, such as the images shown in FIGS. 8B, 11, 13A-13D, and 14A-14B may not be displayed anywhere in the system.

The system may configure the camera processors upon initiation of the system. For example, information from the server can be downloaded to the camera processors upon initiation of the system. This information may be location specific parameters relating to the layout of the clinical environment. Such information may include the location of the entrance and exit, the location of the patient's bed, the location of the display devices, the location of the cameras and the location of a handwashing area. After configuration of the camera processors upon initiation of the system, the system may operate as a distributed monitoring system wherein the cameras and associated processors may not rely on the server. Advantageously, a distributed monitoring system does not present a single source of failure. For example, the system may continue to operate even if the server and/or an individual camera and associated processor fail to operate properly.

The processors associated with each camera may process the images and frames from the camera. Thus, the images and frames may be processed locally on each camera and may not be transmitted or sent to a central point such as the server. For example, the images and frames may be processed on each processor associated with the camera to obtain processed data such as trackers, information relating to boundary boxes, and IDs. In some embodiments the processed data may not be sent to a central point such as the server but may be further processed by the processor locally on each camera. Thus, each clinical environment or subset thereof may be monitored individually without a need to transmit data, such as raw images and frames or processed data such as boundary boxes and IDs, between processors or to a central point such as a server.

The processors may generate an alert or warning, for example to warn that a contaminated person is near a patient's bed, as described herein. The generated alert or warning may be based on processed data from the processor such as boundary box coordinates as described herein. The processor may transmit the alert or warning to a display device. The display device may be the display closest to where the activity of interest has occurred or is occurring, for example a contaminated person near a patient's bed. The processor may determine the display device closest to the activity of interest, and thus the display to which it may transmit an alert, based upon an initial configuration of the processor with location specific parameters relating to the layout of the clinical environment.

Optionally, non-image data may be sent to the central server 108. Data sent to the central server 108 can include, for example, coordinates of the outline instead of the actual image of the individuals and other non-image information. The transmitted data can be sent to the central server 108 for storage purposes. The raw images may never be transmitted to a central server so as to reduce risks of violation of confidentiality and/or privacy. Sending the processed data can also reduce the need for a large bandwidth, which is necessary for sending the images captured by the camera, which have a much large file size than the processed data sent by the system disclosed herein.

The system disclosed herein require as little as a single hit of a person on a camera for positive identification of the person. Once identified by the system, the person can be tracked around the clinical setting and be identified when the person shows up in any camera image of the system 10. Any individuals present at the clinical setting can be issued an identification tag. The clinicians and/or patients can be issued a relatively long-term tag. A visitor can optionally be issued a temporary tag. The video monitoring function of the system can identify a person or an object in the image by a face recognition module, identification of the tag, and/or both methods. For example, when a clinician is wearing a mask, there may not be sufficient information on the exposed portion of the clinician's face to allow the face recognition module to identify the clinician. The person's face can also be otherwise obscured partially or completely, such as when the person's arms are blocking at least a portion of the face. In those cases, the system can identify the person using the identification tag.

The clinical activities that can be detected by the system 10 can include, but are not limited to, objects and/or people of interest, actions of interest, and/or the like. To detect people and/or objects of interest, the system can use a shape, pose, facial features, and/or other distinguishing features. As will be described in greater detail below, the system 10 can include a facial recognition module, which may extract unique facial features of an individual, and/or electronic ID readers for reading an ID tag worn by the individual. The ID tag can be an RFID tag, a Bluetooth or Bluetooth Low Energy, also known as "BLE" (for example, by having two Bluetooth receivers in the camera) tag, a barcode, a QR code, and/or the like. The system 10 can also include modules for extract unique features within an object, for example, using RFID tags, QR codes, barcodes, unique fiducial tags, or otherwise. The system 10 can also match detected features of a person or object with stored objects for detection purposes. The database maintained on the server 108 can include a database of features over a short period of time. The database of features may be made to be not re-identifiable by a human observer of the stored features so as to reduce or avoid the need of long term storage, which may cause privacy concerns. The system 10 can also include a depth camera to confirm that a face detected by the facial recognition module is a face of a real person rather than an image or photo of a face.

To detect and/or identify actions of interest, the system can monitor multiple spatially and/or temporally related frames of the video images. The system can associate action detector outputs with the identified objects. An action or activity detector can include detecting an activity vector. The system can identify a sequence of actions using the activity vectors. Machine learning features can be used to train the systems disclosed herein to detect certain clinical activities or any other activities. As a non-limiting example, a convolutional neural network ("CNN") of the system can run a plurality of times, for example, 20, 30, 40 times, or otherwise, during detection of a handwashing activity, to output a vector after each run. Each vector can include 128 numbers in each step. A matrix of data can be formed from the vectors. The system can analyze the matrix to determine whether handwashing has occurred. The outputs of the CNN are strung together to form a recurrent neural network. Different temporal component for different parts of a handwashing activity can be detected to more accurately determine that handwashing has occurred. For example, if an identified clinician is detected as having moved to within a certain distance from a sink, turned on the water, rinsed hands with running water, lathered hands with soap, and/or rinsed off soap with water, the system can detect a handwashing action by the clinician. The system can also detect different types of handwashing with different durations, for example, handwashing with water lasting no more than about 6s, handwashing with an antibacterial solution lasting about 8s to about 10s, handwashing with soap lasting about 20s to about 1 minute, surgical scrub lasting about 5 minutes to about 10 minutes, and other durations. The system may potentially track clinical activities across multiple cameras, as will be described in more details below.

The system 10 can also evaluate the sequence of object-action interactions to predict potential interactions, for example, through occlusions. The system 10 can output alerts and/or reports to a user. The system 10 can also require immediate feedback in certain cases, for example, when the clinician failed to wash his or her hands before touching a patient.

Figure 1B:
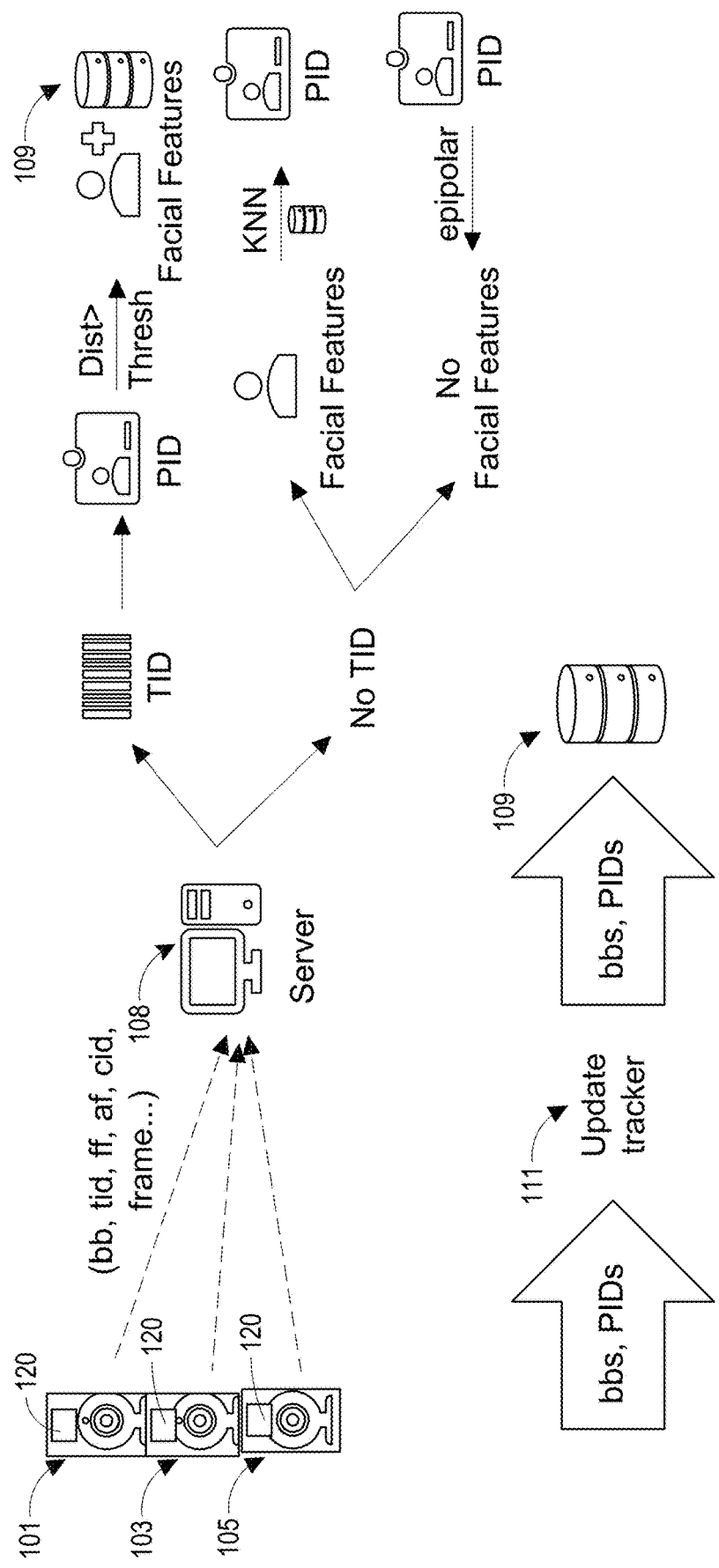
FIG. 1B is a block diagram illustrating algorithms run in an example clinical activities monitoring system.

As shown in FIG. 1B, the cameras 101, 103, 105 can each include a processor 120 to process raw images into non-image data as described above. The cameras 101, 103, 105, which can be the plurality of cameras (for example, Camera 1 100, Camera 2 102, Camera 3 104 . . . up to Camera K 106) of the system 10 in FIG. 1A, can transmit a plurality of non-image data to the central server 108 via the processor 120. The non-image data can include, for example but not limited to, boundary box ("bb") coordinates, tag identifier ("tid") information, extracted facial features ("ff") from convolutional neural network (CNN), activity features ("af"), camera identifier ("cid") information, unique ID for each person, such as of the clinician, ("pid"), frame number, and/or others.

The server 108 can use the following logic to process the non-image data in a given frame. If an identification tag is identified, that is, if tag identifier information is received by the server 108, the server 108 can output the unique ID for each person, pid, based on the tag identifier information. If the server 108 has also received extracted facial features, ff, the server 108 can determine whether a distance of the extracted facial features to all other facial features of the identified person, which are stored in the database 109 of the server 108, is greater than a predetermined threshold. Exceeding the threshold can indicate that the previously extracted facial features of this person is outdated (for example, if the person's face has put on or lost weight, has aged, and/or otherwise). If the threshold is exceeded, the extracted new facial feature is used to update the facial features of that person in the database 109. If the threshold is not exceeded, the facial features stored in the database 109 is still up to date and are not updated.

If no tag identifier information is received by the server, the server 108 can determine whether extracted facial features, ff, have been received. If extracted facial features, ff, have been received, the server 108 can use the k-nearest neighbor ("KNN") algorithm or another pattern recognition algorithm to find a matching unique ID of the person, pid, stored in the database 109 by comparing the received extracted facial features, ff, with the store facial features that are associated with that pid. If no extracted facial features have been received, the server 108 can attempt to assign a unique ID of the person based on the epipolar geometry of the person's location in the frame. If the attempt is not successful, the server 108 can assign a negative ID to the person.

As shown in FIG. 1B, after associating the boundary boxes with pids of the people, the server 108 can update the trackers 111 on the server with the newly detected pairing of the boundary boxes and pids of people, for example, by creating a new tracker for each of the detected boundary boxes and/or pids. The server 108 can also push the information from the updated trackers 111 to the database 109. The database 109 can update the identification of the detected people, their locations, and/or activities using the updated trackers. The database 109 can store only the latest information about the detected people after processing the combined information from the updated trackers, for example, if the person has moved to a new location, the person's identification has been revised, the person has performed a monitored activity such as handwashing, and/or the like.

Figure 1C:
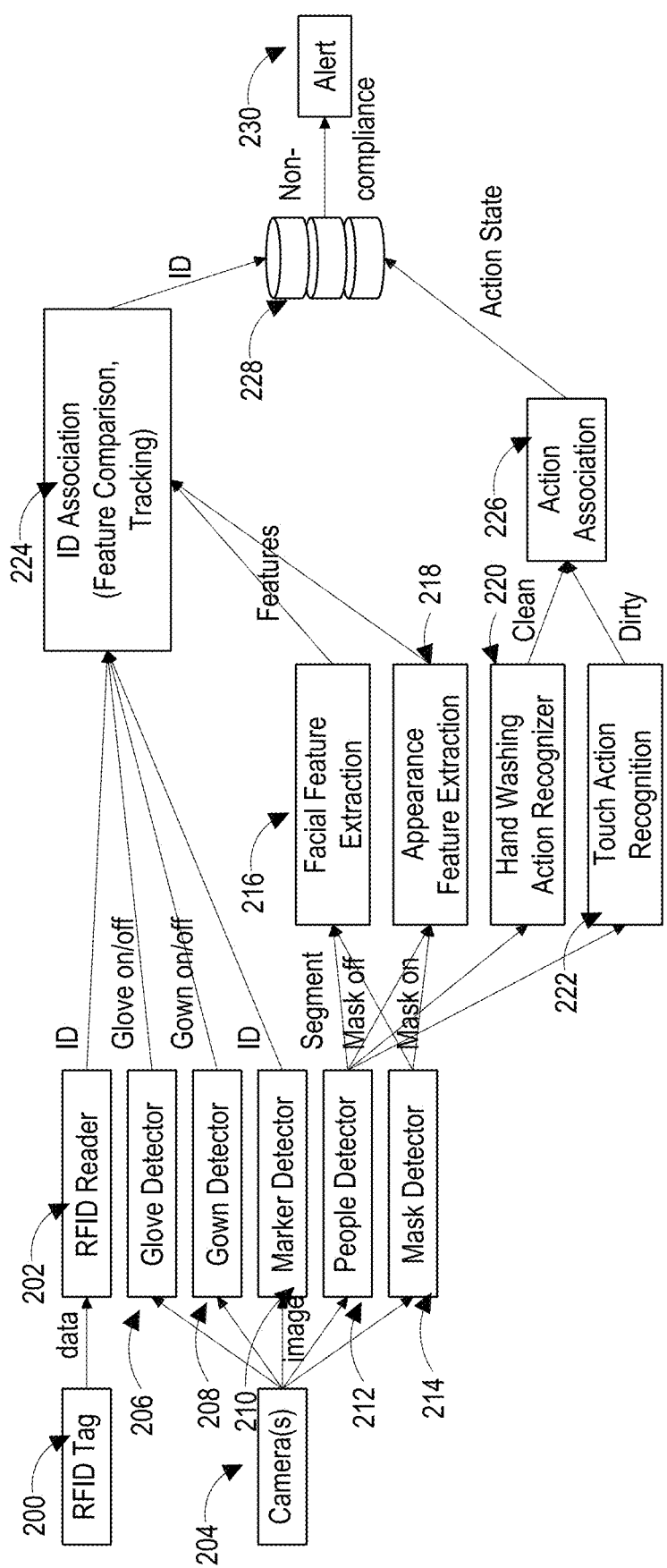
FIG. 1C is a block diagram showing functions of the various hardware and software components of an example clinical activities monitoring system.

FIG. 1C illustrates interactions of the different hardware and software components of the clinical activities monitoring system. The optional RFID tag 200 can include data that can be read by the RFID reader 202. The RFID tag can be replaced by a BLE tag or a color-coded tag, or otherwise. The ID information can be sent to an ID association module 224 to identify inanimate objects and/or people (in particular, when the people's faces are at least partially occluded). The one or more cameras 204, which can be the cameras as shown in FIGS. 1A and 1B, can include a plurality of detector modules in their respective camera processors. Glove detector 206 and/or gown detector 208 can be used to detect whether the gloves and/or gown are worn and/or taken of, which can be sent to the ID association module 224. A marker detector 210 can detect an identification marker placed on any object of interest, for example, sink, hand sanitizing station, and/or the like. The ID information from the marker detector 210 can be sent to the ID association module 224.

A people detector 212 (such as the facial recognition module and/or the identification tag) can scan segments of a person's face and/or body. A facial feature extraction module 216 can extract facial features from the scanned segments. An appearance extraction module 218 can extract appearance features 218 from the scanned segments. The extracted facial and/or appearance features can be sent to ID association 224. A mask detector 214 of the camera(s) 204 can sense whether a person is wearing a mask or not wearing a mask, which can be sent to the facial feature extraction module 216 and/or the appearance feature extraction module 218. The facial feature extraction module 216 and/or the appearance feature extraction module 218 can extract the information about whether someone is wearing a mask to the ID association module 224.

The ID association module 224 can process all the ID information provided by the detectors and/or feature extraction modules, such as by comparing similar features, and/or tracking of the people. The ID association module 224 and an action association module 226, which will be described below, can be located on the server (such as the server 108 in FIGS. 1A and 1B). The ID association module 224 can determine any non-compliance instances, for example, unauthorized personnel being present in the clinical setting, the clinician not wearing gloves when touching a patient, and/or the like. Any non-compliance instances can be updated to the database 228 and outputted to an alert module 230 to output an alert or warning. In some embodiments, the alert or warning can be outputted to a multi-parameter patient monitoring system nearest to where the non-compliance instance has occurred.

The scanned segments from the people detector 212 can also be sent to a handwashing action recognizer module 220 for recognizing handwashing actions 220 and/or to a touch action recognizer module 222 for recognizing touch actions. When a handwashing action is recognized, the handwashing action recognizer module 220 can output that the hands of the person are clean to an action association module 226. When a patient touch action is recognized, the touch action recognizer module 222 can output that the hands of the clinician, visitor, or otherwise, are contaminated to the action association module 226. The system can also include other types of action recognizer modules, such as for monitoring injection actions to improve patient safety.

The action association module 226 can process the action information provided by the handwashing and touch action recognizer modules 220, 222. The action association module 226 can determine any non-compliance instances. Any non-compliance instances can be updated to the database 228 and outputted to the alert module 230 to output an alert or warning. In some embodiments, the alert or warning can be outputted to a multi-parameter patient monitoring system nearest to where the non-compliance instance has occurred.

Example Systems for Handwashing Detection

Figure 2A:
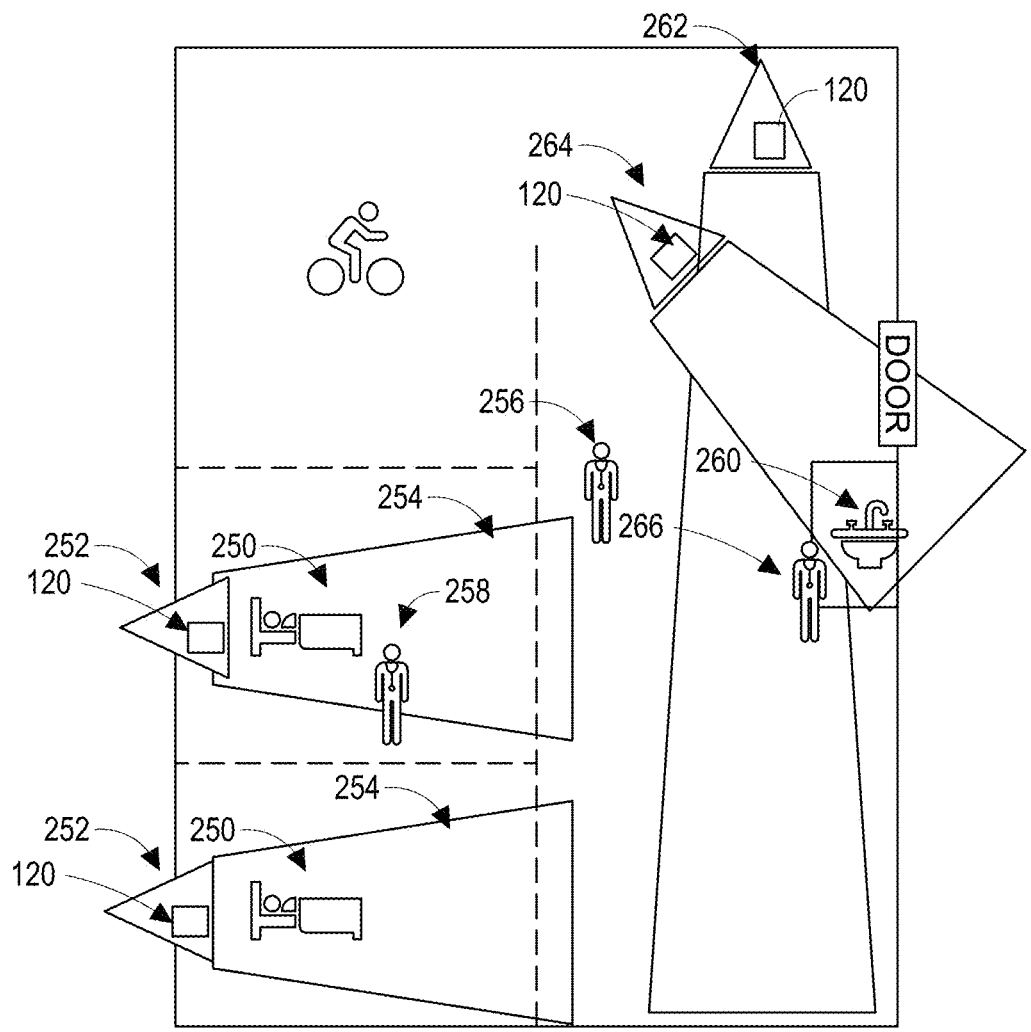
FIG. 2A is a schematic drawing showing an example clinical activities monitoring system configured to detect non-compliance instances of hand hygiene.

An example of touch and handwashing action detection will be described with reference to FIG. 2A. As shown in FIG. 2A, in a clinical setting, such as a hospital, the hospitalized patients can be lying on hospital beds 250. Each hospital bed can be equipped with a camera 252 near a head side of the bed looking toward a foot side of the bed. The hospital can include a handwashing area 260. In some implementations, such as shown in FIG. 2A, a far camera 262 and a near camera 264 can be directed to generally face the same area, such as toward the handwashing area 260. Each of the far camera 262 and the near camera 264 can include a camera processor 120. The processor 120 of the far camera 262 can process images of a scene encompassing at least partially the handwashing area 260. The near camera 264 can capture more focused, higher-resolution images of at least partially the handwashing area 260, which can be processed by the processor 120 of the near camera 264. The combination of the far camera 262 and the near camera 264 can cover substantially an entirety of the handwashing area 260. The arrangement of the far camera and the near camera can also aid in resolving ambiguities in the images captured by one of the far and near cameras 262, 264.

As shown in FIG. 2A, the processor 120 on the camera 252 can detect whether the clinician (or a visitor) is within a patient zone, which can be located within a field of view 254 of the camera 252. A patient zone can be defined as a hospital bed (with or without a patient in the bed) and/or the patient. In some embodiments, the clinician is within the patient zone if the clinician is at least partially within a proximity threshold to the hospital bed and/or the patient. In the illustrated example of FIG. 2A, the person 256 is outside the field of view 254 of the camera 252 or the field of view of the far camera 262 or the near camera 264, and therefore cannot be detected by any of the cameras in FIG. 1A. The person 258 is within the field of view 254 of the camera 252. As disclosed herein, the person 258 can be identified in a variety of manners, for example, as described above with reference to FIG. 1B.

If the processor 120 on the camera 252 detects that a clinician is within the patient zone and/or has touched the patient, the server (not shown in FIG. 2B) that is in electrical communication with the processor 120 of the camera 252 can determine that the clinician has been contaminated. In some embodiments, the processor 120 on the camera 252 can detect a touch action by detecting the actual act of touching by the clinician on the patient and/or by the clinician being in close proximity, for example, within less than 1 foot, 6 inches, or otherwise, of the patient.

If the contaminated clinician, for example, the person 256, moves outside the patient zone in which lies the patient touched by the clinician (for example, when a clinician just left a patient after touching the patient), the processor on the camera and/or the server can assign a contaminated ++ or similar status to the clinician. If the contaminated ++ clinician re-enters the same patient zone or enters a new patient zone, the server can output an alarm or warning. In some embodiments, the alert or warning can be outputted by the server to a multi-parameter patient monitoring system nearest to where the contaminated ++ clinician is located.

If the processor 120 on the far camera 262 and/or the near camera 264 detects a handwashing activity (as described above) by a contaminated ++ clinician 266, the processor on the camera and/or the server can reassign a "not contaminated" or similar status to the clinician 266.

For each detected clinician (such as physician, nurse, and/or the like), the non-compliance instances detection method disclosed herein can be looped through each of the detected patients. The system can reduce the likelihood of false positives (that is, a clinician who has not touched a patient but is assigned a contaminated ++ status) so as to not overburden the clinician with the handwashing alerts.

Figure 2B:
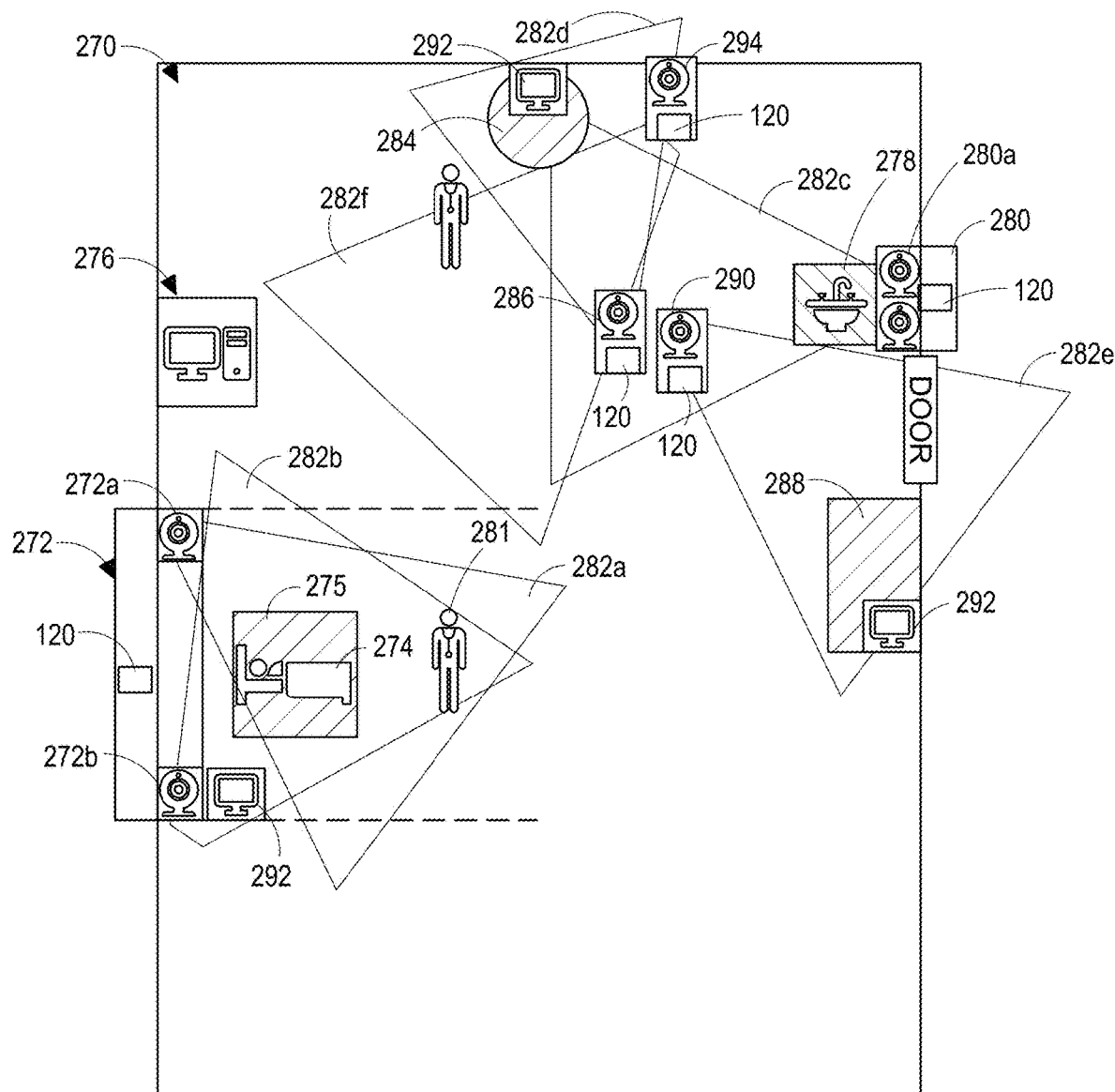
FIG. 2B is a schematic drawing of an example clinical activities monitoring system configured to detect non-compliance instances of hand hygiene.

FIG. 2B illustrates an example clinical activities monitoring system 270 that is in a clinical setting and that is configured to detect clinical activities such as handwashing. The system 270 can include a plurality of cameras, for example, about six cameras or more. The cameras can be parameterized based on the location and/or use of the cameras. The cameras can be configured, including but not limited to being installed at a height and/or angle, to detect a person's face and/or identification tag, if any. For example, at least some of the cameras can be installed at a ceiling of the room or at a predetermined height above the floor of the room. The cameras can be configured to prioritize detection of the identification tag. Alternatively, the cameras can be configured to prioritize detection, which can include extracting facial recognition features of the detected face, and/or to run the detection of the face and the identification tag substantially simultaneously.

As shown in FIG. 2B, the clinical setting can be a room in a hospital with one or more hospital beds 274. Two bed cameras 272a, 272b can be placed on two sides of the hospital bed 274. The bed cameras 272a, 272b can be located above a head side of the bed 274, where the patient's head would be at when the patient lies on the bed 274. The bed cameras 272a, 272b can be separated by a distance, which can be wider than a width of the bed 274, and can both be pointing toward the bed 274. The fields of view 282a, 282b of the bed cameras 272a, 272b can overlap at least partially over the bed 274. The combined field of view 282a, 282b can cover an area surrounding the bed 274 so that a person standing by any of the four sides of the bed 274 can be in the combined field of view 282a, 282b. The bed cameras 272a, 272b can each be installed at a predetermined height and pointing downward at a predetermined angle. The set-up of the bed cameras 272a, 272b can be configured so as to maximize the ability of that at least one of the bed cameras 272 detecting the face of a person standing next to or near the bed 274, independent of the orientation of the person's face, and/or the ability to detect an identification tag that is worn on the person's body, for example, hanging by the neck, the belt, etc. Optionally, the bed cameras 272a, 272b need not be able to detect the patient lying on the bed 274, as the identity of the patient is typically known in the clinical setting. In some embodiments, the bed cameras 272a, 272b can be installed and/or oriented symmetrically about the bed 274.

The bed cameras 272a, 272b can be coupled to a shared processor 120. The bed cameras 272a, 272b and the processor 120 can form a first imager 272. Alternatively, the bed cameras 272 can each include a processor 120. The processor(s) 120 of the first imager 272 can process the images from both the bed cameras 272a, 272b and send processed data based on those images to a server 276, which can be in electrical communication with the processor 120 of the first imager 272. The server 276 can be located in the hospital room, or elsewhere in the hospital, or at a remote location outside the hospital. The processor 120 of the bed cameras 272 can detect whether the clinician (or a visitor) is within a patient zone, which can be located within the fields of view 282a, 282b. A patient zone can be defined as a hospital bed (with or without a patient in the bed) and/or the patient. In some embodiments, the clinician is within the patient zone if the clinician is at least partially within a proximity threshold to the bed 274, such as the shaded area 275 around the bed 274, and/or of patient. Although the cameras 272a, 272b can detect a person 281, who is inside the fields of view 282a, 282b, the processor 120 of the first imager 272 is configured to determine that the person 281 is not in the patient zone 275. If the processor 120 of the first imager 272 determines that a person has entered the patient zone 275 and/or has touched the patient, the server 276 can determine that the person is now contaminated.

A person may also be contaminated by entering contaminated areas other than a patient zone. For example, as shown in FIG. 2B, the contaminated areas can include a patient consultation area 284. The patient consultation area 284 can be considered a contaminated area with or without the presence of a patient. The system 270 can include a consultation area camera 286, which has a field of view 282d that overlaps with and covers the patient consultation area 284. The consultation area camera 286 can include its own processor 120 to form a second imager. The contaminated areas can further include a check-in area 288 that is next to a door of the hospital room. Alternatively and/or additionally, the check-in area 288 can extend to include the door. The check-in area 288 can be considered a contaminated area with or without the presence of a patient, under the assumption that a person just checked into the room is likely contaminated. The system 270 can include an entrance camera 290, which has a field of view 282e that overlaps with and covers the check-in area 288. The entrance camera 290 can include its own processor 120 to form a third imager.

The hospital room can include a handwashing area 278, such as an area surrounding a sink as shown in FIG. 2B. The system 270 can include two handwashing cameras 280a, 280b directed at the handwashing area 278. Alternatively, the system 270 can include a different number of cameras directed at the handwashing area 278. The handwashing cameras 280a, 280b can be mounted behind the handwashing area 278, for example, on the wall behind the sink, to have a combined field of view 282c so as to maximize the ability to detect a person's face and/or identification tag when the person is standing next to the handwashing area 278 facing the sink.

The handwashing cameras 280a, 280b can be coupled to a shared processor 120. The handwashing cameras 280a, 280b and the processor 120 can form a fourth imager 280. Alternatively, each of the handwashing cameras 280 can include its own processor 120. As will be described in more detail below, the processor 120 can process images from one of the handwashing cameras 280a, 280b, which can be designated as the primary camera, before processing images from the other handwashing camera 280, which can be designated as the secondary camera. Having a primary handwashing camera and a secondary handwashing camera can allow monitoring of handwashing activities in case one of the handwashing cameras 280 fails to detect the handwashing activities at the handwashing area 278. In some implementations, the handwashing cameras 280a, 280b can be mounted at different heights. For example, the lower one of the handwashing cameras 280a, 280b may be better at detecting an identification tag worn by the person at the handwashing area 278 and the higher one of the handwashing cameras 280a, 280b may be better at detecting the face of the person standing at the handwashing area 278a. The lower one of the handwashing cameras 280a, 280b can be designated as the primary camera and the higher one of the handwashing cameras 280a, 280b can be designated as the secondary camera, or vice versa. Additionally and/or alternatively, the lower one of the handwashing cameras 280a, 280b, being closer to the faucet, can be configured to detect a handwashing activity and the higher one of the handwashing cameras 280a, 280b can be configured to detect the face and/or identification tag of the person entering the handwashing area 278.

The processor 120 of the fourth imager 280 can transmit processed data from the images in the handwashing cameras 280a, 280b to the server 276, which is in electrical communication with the processor 120 of the fourth imager 280. As noted above, if the server 276 has received processed data from the processor 120 of the first imager 272, the second imager 286, the third imager, or any other imager that a clinician is within a contaminated area and/or has otherwise touched the patient, the server 276 can determine that the clinician has been contaminated. If the contaminated clinician moves outside the contaminated area in which the clinician became contaminated, and the processor 120 of the fourth imager 280 detects that clinician entering the handwashing area 278, the processor 120 of the fourth imager 280 can further determine whether the clinician has washed his or her hands at the sink. The processor 120 of the fourth imager 280 can use any of the handwashing detection methods disclosed herein, for example, by the duration of the clinician in the handwashing area 278, whether the contaminated clinician is detected as being within a certain distance from the faucet, having turned on the water, rinsed hands with running water, lathered hands with soap, and/or rinsed off soap with water, or otherwise. The server 276 can change the status of the clinician from contaminated to clean after receiving data from the fourth imager 280 that the clinician has performed the handwashing action.

If one of the imagers of the system 270 detects the contaminated clinician entering the same or a different contaminated area before detection of a handwashing activity of the contaminated clinician by the fourth imager 280, the server can output a warning. In some embodiments, the alert or warning can be outputted by the server 276 to a multi-parameter patient monitoring system 292 nearest to where the non-compliance instance has occurred, that is, where the contaminated clinician is located. As shown in FIG. 2B, the system 270 can include a plurality of multi-parameter patient monitoring systems 292, which can be in electrical communication with the server 276. An example of such a multi-parameter patient monitoring system 292 is the Root® platform of Masimo Corporation (Irvine, CA). The multi-parameter patient monitoring systems 292 can be placed at any locations in the hospital room, for example, by the bed 274, at the patient consultation area 284, at or near the check-in area 288, or others. Preferably at least one of the multi-parameter patient monitoring systems 292 is placed at or near each contaminated area.

As shown in FIG. 2B, the system 270 can further include additional imagers, such as a fifth imager including a camera 294 including its own processor 120, and/or otherwise. These additional imagers may not be directed to any specific contaminated and/or handwashing areas. For example, the camera 294 of the fifth imager can have a field of view 282f that covers substantially an area that a person likely has to pass when moving from one area to another area of the hospital room, for example, from the patient zone 275 to the consultation area 284. Such additional imagers can provide processed data to the server 276 to facilitate tracking of movements of the people in the room.

Figure 2C:
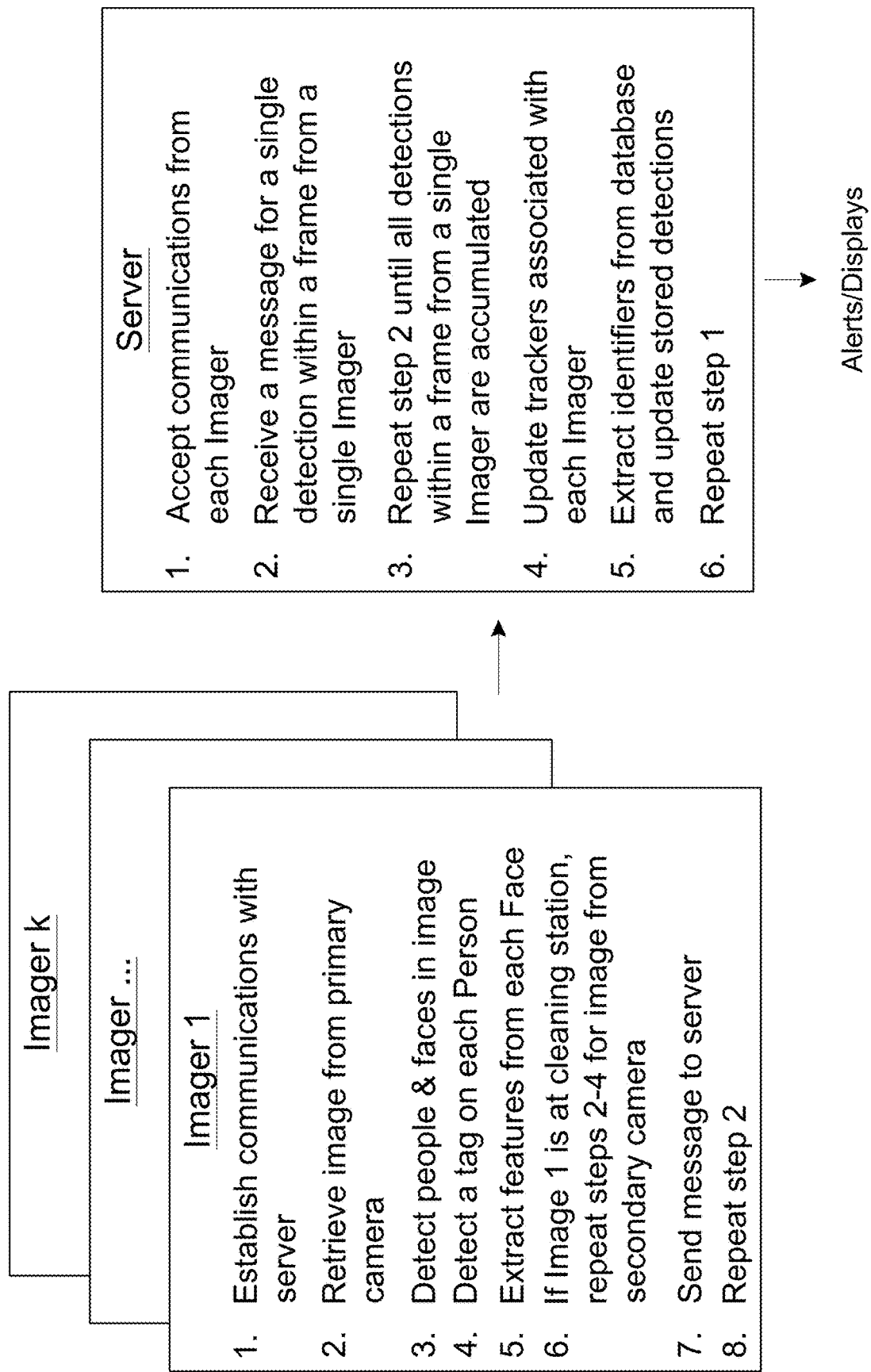
FIG. 2C illustrates example processes of the clinical activities monitoring system in FIG. 2B.
Figure 2C:
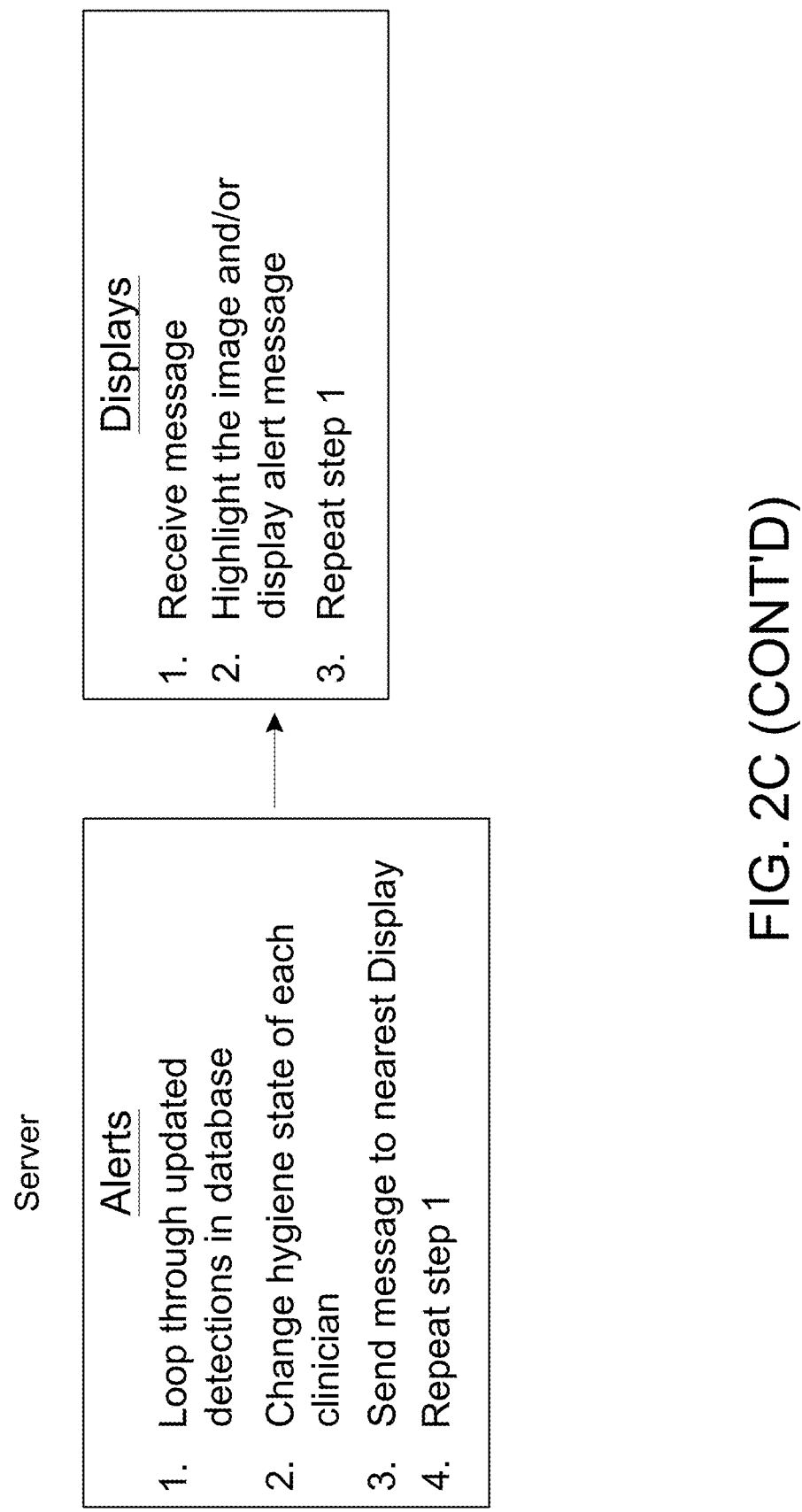

FIG. 2C illustrates example processes implemented by the processors of the system 270. The processor 120 of one of the imagers in the system 270, which can be coupled to a single camera or two cameras (or more), can carry out the following steps. At step 1, the processor 120 can establish communication with the server 276. At step 2, the processor 120 can retrieve an image captured by its respective camera. If the processor 120 is the processor 120 of the fourth imager 280, the processor 120 can retrieve an image from the primary camera. If the processor 120 is the processor 120 of the first imager 272 or any other imager that includes two cameras, the processor 120 can capture an image of any of the two cameras. At step 3, the processor 120 can detect a person and/or the person's face in the image. At step 4, the processor 120 can detect an identification tag on the detected person. At step 5, the processor 120 can extract the features from each detected face. Preferably, the processor 120 can prioritize detection of the identification tag, which can be faster, more accurate, and/or less computation intensive, over the extraction of facial features. At an optional step 6, if the processor 120 is coupled to more than one camera, the processor 120 can repeat steps 2 to 4 or steps 2 to 5 on receive an image from the other camera(s) of the imager. The images captured by the cameras of the imager are obtained from the same time frame. After the processor 120 has processed an image from each camera of the imager, at step 7, the processor 120 can send to the server the processed data, which can include, inter alia, boundary box ("bb") coordinates, tag identifier ("tid") information, extracted facial features ("ff") from convolutional neural network (CNN), activity features ("af"), camera identifier ("cid") information, unique ID for each person, such as of the clinician, ("pid"), frame number, and/or others. After having performed step 7, the processor 120 can return to step 2 to capture a new image at a new time frame.

The server 276, which can include a server processor that is separate from the camera processors described above, can perform the following steps. At step 1, the server 276 can accept a request to establish communication from each imager of the system 270. At step 2, the server 276 can receive a message, or processed data, of a single detection within the specific time frame from a single imager. A detection can be a detection of a person's presence, the person's identification tag, the person's extracted facial features, and/or the person's movement or action. At step 3, the server 276 can repeat step 2 until the detections within that time frame from that imager has been accumulated. At step 4, the server 276 can update the trackers associate with each imager. A tracker can be created for each detection of a camera or imager. At step 5, the server 276 can extract identifiers from a database located at the server or elsewhere and update identification, location, and/or activity status of each detected person based on the updated trackers from step 4, that is, from the detections of all the cameras or imagers. Accordingly, as noted above, the database only keeps at a global level the latest identification and/or activity of the detected person based on the combined information from the updated trackers. For example, if the database has previously stored a person's identification, which the server 276 later determines to be an erroneous identification based on later updated trackers, the database can discard the erroneous pervious identification, and store the new identification of the detected person. An erroneous identification can be made, for example, when the previous identification was based on the extracted facial features and the later identification was based on a detected identification tag that was not detected during the previous identification. If the person is determined to have moved from one area to another area in the hospital room based on the detections from different imagers, the server 276 can retrace and/or estimate where the detected person has been. The database can discard the previous location information and store the latest location of the detected person. The server 276 can then return to step 1 to communicate with the next imager, until processed data has been transmitted by every imager of the system 270 to the server 276.

In addition to updating the database, the server 276 can also implement an alert program. As shown in FIG. 2C, at step 1 of the alert program, the server 276 can loop through the updated detections in the database. At step 2, the server 276 can change the hygiene state of each person, such as clinician, if such change has been determined as disclosed herein. At step 3, if the person is still contaminated when entering a contaminated zone, the server 276 can output an alert message to the nearest display device, which can be the display device of a multi-parameter patient monitoring system 292 of the system 290. The server 276 can determine the nearest display device by locating the imager that has detected the person's latest whereabouts. The server 276 can return to step 1 to look for the next contaminated person who is entering a patient zone.

As shown in FIG. 2C, the display can have its own processor, which can be a processor of the multi-parameter patient monitoring system 292. The processor of the display can perform the following steps when an alert message is sent by the server 276. At step 1, the display can receive the alert message from the server 276. At step 2, the display can highlight, for example, by flashing or otherwise, a displayed image and/or display the alert message. The display can optionally output an audio message in response to the alert message from the server 276. The display can repeat the two steps in response to any subsequent alerts. In some embodiments, after the contaminated person has left the contaminated zone, that nearest display can be instructed by the server 276 to stop displaying the alert message.

Figure 3A:
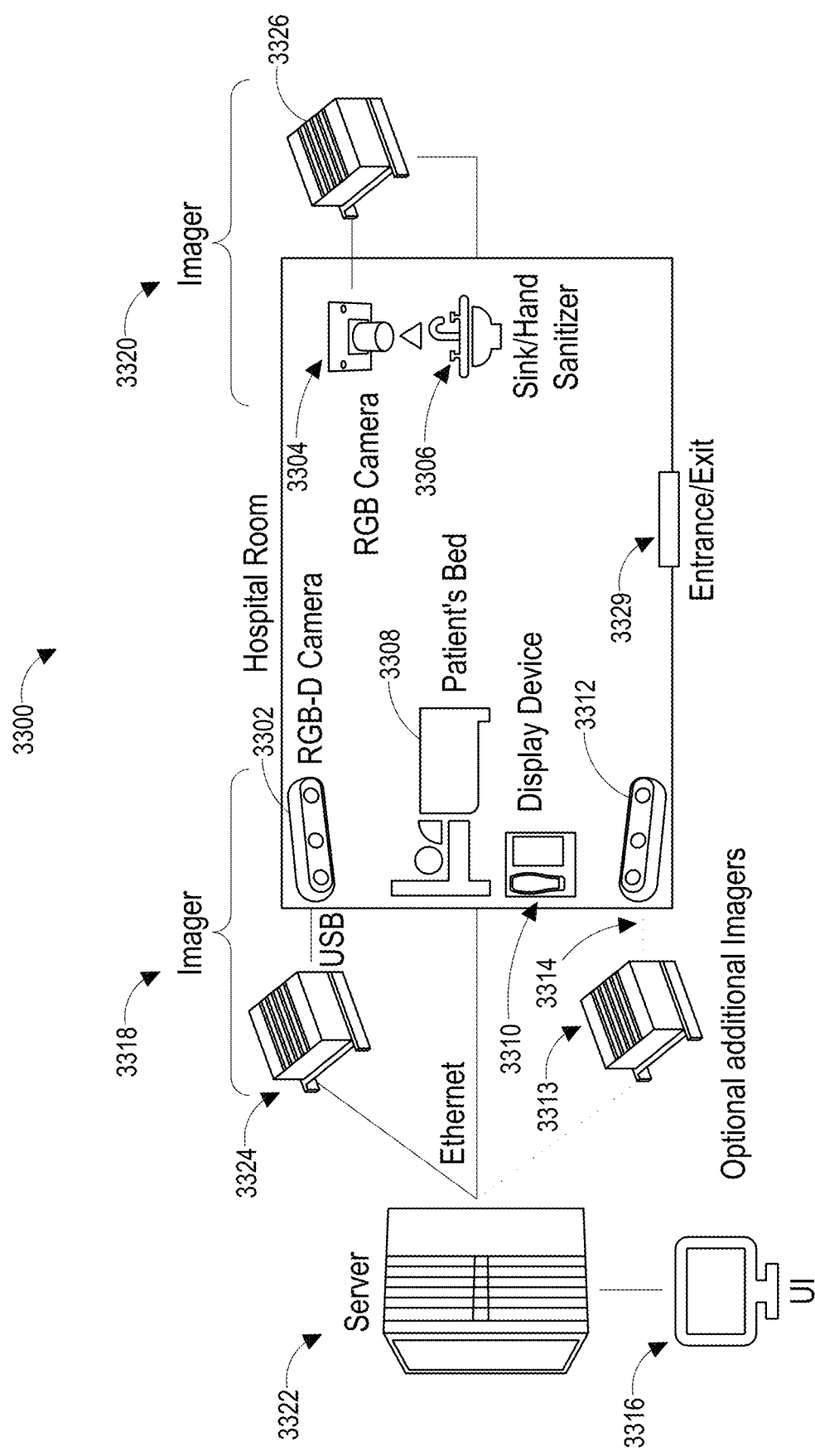
FIG. 3A illustrates schematically an example hand hygiene compliance monitoring system.
Figure 3C:
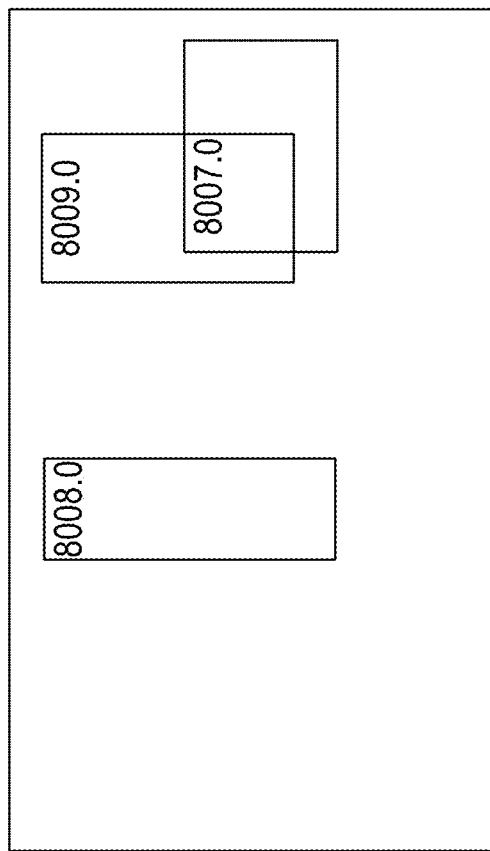
FIG. 3C illustrates an example processed data corresponding to the raw image of FIG. 3B.

FIG. 3A illustrates an example hand hygiene compliance monitoring system 3300 in a clinical setting. The system 3300 may monitor the activities of anyone present in the room such as medical personnel, visitors, patients, custodians, etc.

The system 3300 may be located in a clinical setting such as a hospital room. The hospital room may include one or more patient beds 3308. The hospital room may include an entrance/exit 3329 to the room. The entrance/exit 3329 may be the only entrance/exit to the room.

The system 3300 may include one, two or more imagers, for example a first imager or image sensor 3318 and a second imager or image sensor 3320. The imagers may each include a dedicated processor. The processor of the imager may be located in the room, for example, in close physical proximity with its associated camera. The processor of the imager may be located adjacent to, or within a predetermined distance (such as less than about one meter, or less than about 0.5 meter, or less than about 0.3 meter, or less than about 0.1 meter) from the camera. In one implementation, the processors may be any embedded processing unit, such as an Nvidia Jetson Xavier NX/AGX, that is embedded in a housing of the camera. Alternatively, the processor of the imager may be wired to the camera and need not be physically located in the room or be near its associated camera. For example, the processor of the imager may be located in a central location in the clinical room and wired to its associated camera. The processors may include microcontrollers such as ASICs, FPGAs, etc. The imagers may each include a camera. The camera may be in electrical connection with the processor and may transmit video image data such as images and frames to the processor. The different imagers of the system 3300 can exchange data and state information. The exchange can be facilitated by a database. The database can include various tables, for example, tables of cameras, items, locations, and mapping. The tables can include syntax for creating a data storage structure.

The database can include information relating to the location of items in the room such as cameras, patient beds, handwashing stations, and/or entrance/exits. The database can include locations of the cameras and the items in the field of view of each camera. The database can further include the setting of each camera. Each camera in the room may include a unique IP address. The processor may provide the IP address of the associated camera, to the server, for example the processor may transmit the IP address to the database. The server may use the IP addresses provided by the processors to identify the cameras and/or the camera locations and to identify what information to transmit to the processor, for example upon initial configuration of the system. For example, prior to starting up the system, all the cameras may have identical configurations. The processors may include code as discussed herein. The code used on each processor may be identical to the code on all other processors. The processor associate with each camera may provide the IP address of its associated camera to the server upon initial configuration of the system. The server may use the IP address to determine which information database and/or database tables to download to the processor upon initial configuration. This information may include location of items in the room and/or in the field of view of the associated camera as discussed. In this manner, the system and its functionality may be distributed among the various processors.

As shown in FIG. 3A, the first imager 3318 includes a processor 3324 and a camera 3302. The camera 3302 may be a camera capable of sensing depth and color, such as a RGB-D stereo depth camera. The camera 3302 may be positioned in a location of the room to monitor the entire room or substantially all of the room. The camera 3302 may be tilted downward at a higher location in the room. The camera 3302 may be set up to minimize blind spots in the field of view of the camera 3302. For example, the camera 3302 may be located in a corner of the room. The camera 3302 may be facing the entrance/exit 3329 and may have a view of the entrance/exit 3329 of the room.

As shown in FIG. 3A, the second imager 3320 may include a processor 3326 and a camera 3304. The camera 3304 may be a RGB color camera. Alternatively, the camera 3304 may be an RGB-D stereo depth camera. The camera 3304 may be installed over a hand hygiene compliance area 3306. The hand hygiene compliance area 3306 may include a sink and/or a hand sanitizer dispenser. The camera 3304 may be located above the hand hygiene compliance area 3306 and may look down on the hand hygiene compliance area 3306. For example, the camera 3304 may be located on or close to the ceiling and may view the hand hygiene compliance area 3306 from above.

In a room of a relatively small size, the first and second imagers 3318, 3320 may be sufficient for monitoring hand hygiene compliance. Optionally, for example, if the room is of a relatively larger size, the system 3300 may include any number of additional imagers, such as a third imager or image sensor 3314. The third imager 3314 may include a processor 3313 and a camera 3312. The camera 3312 of the third imager 3314 may be located near the patient's bed 3308 or in a corner of the room, for example, a corner of the room that is different than (for example, opposite or diagonal to) the corner of the room wherein the camera 3302 of the first imager 3318 is located. The third camera 3312 may be located at any other suitable location of the room to aid in reducing blind spots in the combined fields of view of the first camera 3302 and the third camera 3312. The camera 3312 of the third imager 3314 may have a field of view covering the entire room. The third imager 3314 may operate similarly to the first imager 3318 as described.

The system 3300 may include one or more display devices 3310. The display devices may be a display of any bedside monitor or other patient monitoring device. For example, the display device can include the Root® and/or Uniview® platforms of Masimo Corporation (Irvine, CA). The display device 3310 may be in communication with the processors and/or the server.

The system 3300 may include a server 3322. The server 3322 may host the database described above and a graphical user interface (GUI) 3316. The imagers in the room may be connected to a server 3322. The server 3322 may be a remote server. The connection can be via Ethernet or any other suitable communication protocols. The imagers and server may communicate via UDP (User Datagram Protocol) message passing.

Optionally, the system 3300 may be integrated with a real time locating service (RTLS) for more accurate recognition and localization. Although the system 3300 is described herein for monitoring hand hygiene compliance, the system may also be used for other types of clinical activities, patient safety monitoring, and/or access control.

Figure 3B:
FIG. 3B illustrates an example raw image captured by a camera of the system of FIG. 3A.

Raw data from the cameras of each imager, for example, the camera 3302, the camera 3304, and optionally the camera 3312, can be transmitted to the associated processor of that imager, for example, the processor 3324, the processor 3326, and optionally the processor 3313. Raw data may include, for example, video image data, raw images, frames, and the like. FIG. 3B illustrates an example raw image frame captured by one of the cameras of the system 3300. The processor of each imager may process the raw data received from the associated camera of the same imager to obtain processed data. FIG. 3B illustrates an example processed frame corresponding to the raw image frame of FIG. 3A. As shown in FIG. 3B, the processed data may include information relating to boundary boxes surrounding any detected person in the room as shown in FIG. 3A, such as coordinates of the boundary boxes and the state information of the boundary boxes. The processed data never includes any images captured by the camera. Advantageously, the raw images from the camera are processed locally on the processor 3324 and are never transmitted to a central location, such as the server 3322. The GUI 3316 never displays any raw images captured by the cameras of the imagers in the system 3300. Not transmitting the raw images to the server ensures anonymity and protects privacy of the people who come into the field of view of the cameras inside the room.

The processors of the imagers in the room may include machine learning features. A non-limiting example of machine learning features includes deep learning features such as the convolutional neural network (CNN). The CNN may learn and determine what features to extract for identification of a person based on raw images. The CNN may feed the extracted features to a recurrent neural network (RNN) for further processing. Additional details of the deep learning features are described below with reference to FIG. 4. The processors on the imagers may track movements of individuals inside the room without using any facial recognition or ID tracking. This feature allows the processors of the imagers to track an individual's movements even when the identification of the individual is unknown. A person in the room may not be identifiable for various reasons. For example, the person may be wearing a mask so that facial recognition modules may not be able to extract any features. As another example, the person may be a visitor who is not issued an ID tag, unlike the clinicians, who typically wears an ID tag. Alternatively, when the person is not wearing a mask and/or is wearing an ID tag, which can be any form of ID tags disclosed herein, the processors of the imagers may combine the motion tracking with the identification of the individual to further improve accuracy in tracking the activity of the individual in the room. Having the identity of at least one person in the room may also improve accuracy in tracking the activity of other individuals in the room whose identity is unknown by reducing the number of anonymous individuals in the room.

The system 3300 may track one or more people in the room. Each person may be tracked individually with each person being assigned a unique track and/or boundary box. Each imager of the system 3300 may independently track movements of any detected person in the room. The processors of the imagers can also communicate with one another to improve accuracy in tracking, for example, by detecting occlusion of one person by another or by any objects in the room. Additional details of the tracking will be described further below.

In addition to detecting the presence of a person and tracking the person's movement, the camera 3304 may monitor the hand hygiene compliance area 3306. As described in greater detail herein, the processor 3326 may track movements of any detected person to determine whether the person has performed a hand sanitizing and/or hand washing activity before approaching a patient zone. The patient zone may be defined as an area within a predetermined distance (for example, about 2 meters to about 5 meters, or otherwise) from any part of the patient's bed, and/or within a predetermined distance (for example, about 1 meter to about 3 meters, or otherwise) of a known patient of this room. One of the processors of the imagers can monitor compliance with a determined hand hygiene protocol. For example, if a person fails to wash their hands properly, one of the processors of the imagers may generate an alert. The processor may be in communication with one or more display devices 3310 in the room. The processor may transmit the generated alert to the display device 3310.

The display device 3310 may output alerts received from any one of the processors 3324, 3326, 3313. The outputted alert may be any auditory and/or visual signal. The outputted alert may notify people in the room that a person has not complied the hand hygiene protocol. The incompliance can include failure to perform hand hygiene activity before entering a patient zone and/or failure to complete each step of the hand hygiene protocol before entering a patient zone. The outputted alert may provide feedback to people in the room. The feedback can include a message prompting the incompliant person to perform hand hygiene activity before entering the patient zone. The feedback can additionally include advice on how to improve the hand sanitizer and/or hand washing techniques. The outputted alert may serve to prevent undesirable actions such as a contaminated person entering the patient zone.

As described above, the system 3300 may include more than one display device. For example, a display device may be located near a patient's bed 3308 and a display device may be located near the hand hygiene compliance area 3306 or anywhere else in the room. The processor of the imager that has generated the alert may determine which display device is nearest to where an event of hand hygiene incompliance has occurred or is occurring. For example, if a contaminated person has approached a patient's bed within a certain threshold, one or more of the processors may transmit an alert to a display device that is nearest to the patient's bed. This determination may be based at least in part on an initial configuration of the layout of the room and/or coordinates of people in the room. The processors of the imagers can download the layout of the room from the server 3322 upon initiation or at the start-up stage of the system 3300. The processors of the imagers can also download the database from the server 3322 upon initiation or start at the start-up stage of the system 3300. The processors of the imagers may not contact the server 3322 or transmit data to the server 3322 after starting up the system 3300. In some embodiments, one or more of the processors of the imagers may transmit an alert to each of the display devices in the room. Advantageously, the processors of the imagers may transmit signals directly to the display device. This may eliminate a need to transmit the alert to a central location such as the server 3322. In some embodiments, one or more of the processors may transmit an alert to the server, for example, for data storage purposes.

Figure 4:
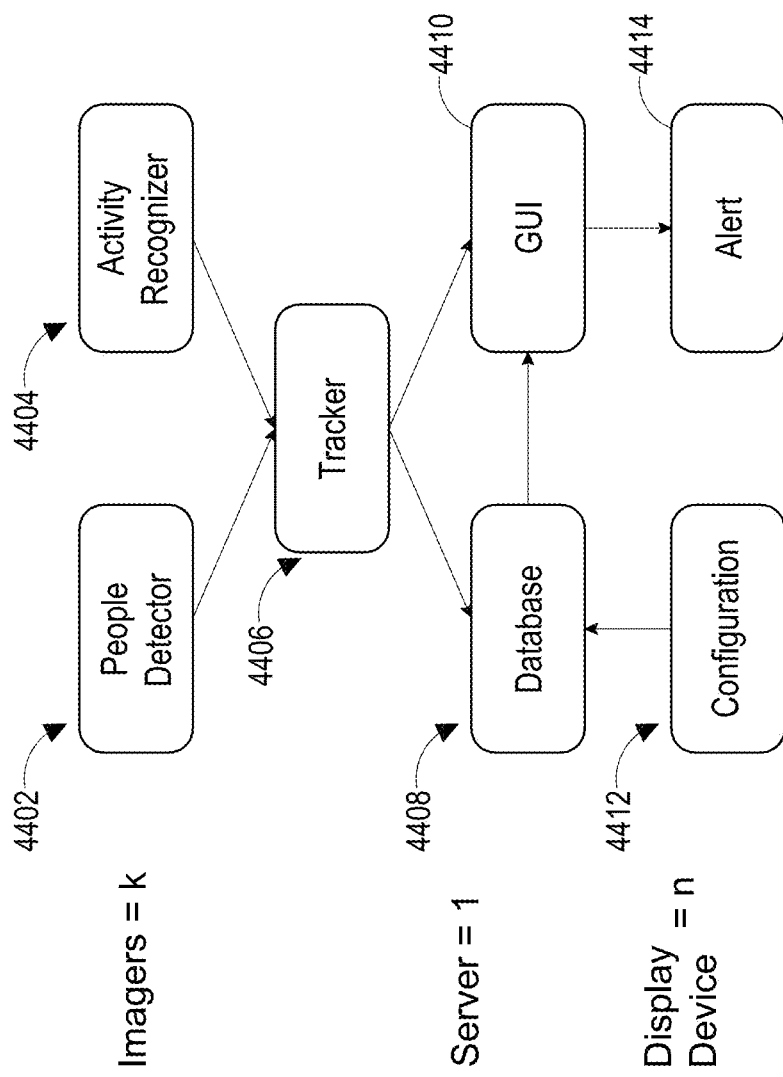
FIG. 4 illustrates a block diagram illustrating various modules and data flow of the monitoring system of FIG. 3A.

FIG. 4 illustrates a block diagram of various modules of the components of the system 3300 to illustrate data flow among the modules. As shown in FIG. 4, the system is distributed across one or more hardware platforms. The hardware platforms may include one or more imagers. The imagers may include various modules such as a people detector module 4402, an activity recognizer module 4404, and/or a tracker module 4406. These modules may include other modules. For example, the activity recognizer module 4404 may include a hand washing activity recognizer module and/or a touch action recognizer module. The output of the people detector module 4402 and the activity recognizer module 4404 can be fed into the tracker module 4406.

The people detector module 4402 can include a program executing on the processor of each imager. The program can receive a frame from the associated camera of the same imager. The program can processes the frame with a YOLO (You Only Look Once) deep learning network, which detects the occurrences of people and returns real-world coordinates of their boundary boxes. The activity recognizer module 4404 can be run on an imager having a camera that is tilted downward at a higher location in the room, for example, the cameras 3302, 3304 shown in FIG. 3A. Each frame from that camera may be processed via an Inception Convolutional Neural Network based deep learning model, which returns a micro action corresponding to an activity, such as hand sanitizing or hand washing. The activity recognizer module 4404 may be trained using a dataset of handwashing or hand sanitizing demonstration videos. Body feature extraction by the activity recognizer module 4404 may be trained on a dataset of people extracted from various sources.

The tracker module 4404 may compare the intersection over union of all boundary boxes in consecutive frames. The tracker module 4404 may associate boundary boxes with a given track (that is, the sequence of boundary boxes associated with a person through consecutive frames) if the boundary boxes of consecutive frames overlap by a predetermined threshold. The tracker module 4404 may assume that boundary boxes from consecutive frames that are adjacent (or the closest with each other) are associated with the same person. Thus, whenever a person detection occurs in the field of view of one camera, that person may be associated with the nearest track, wherever that person moves within the field of view of that camera.

The imagers may be in communication with the server so that the output from the tracker module 4402 can be fed to the database 4408 and the graphical user interface 4410 of the server. The database 4408 may be in communication with the user interface 4410. The configuration 4412 of the display device(s) in the room, for example, the location of the display device(s) can be uploaded to the database 4408. When the processors of the imagers download the database 4408 from the server upon start up on the system, the processors of the imagers can receive the configuration information of all the display device(s) in the room. The information about the display device(s) in the room can aid the processor of the imager to determine to which display device to transmit an alert about hand hygiene incompliance. The user interface 4410 may facilitate configuration of an alert module 4414 of the display device(s).

Figure 5:
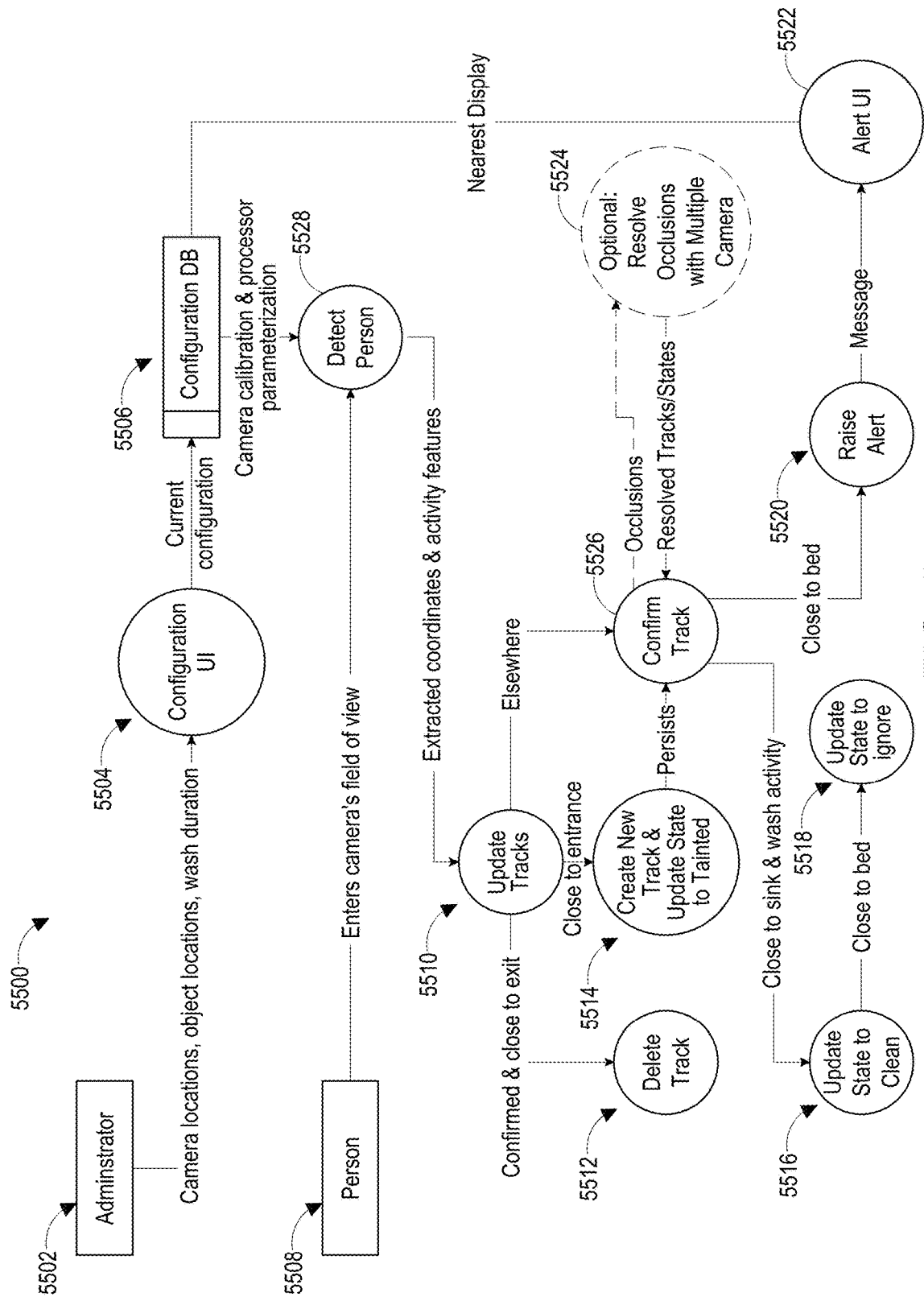
FIG. 5 illustrates an example process of the monitoring system of FIG. 3A.

FIG. 5 illustrates an example process 5500 of the system of FIG. 3A. In this example, an administrator 5502 determines configuration parameters. The configuration parameters may include location-specific parameters such as camera locations, handwashing station locations, patient bed locations, display device locations, entrance/exit locations, other object locations and may also include other parameters such as hand hygiene protocols and the like. The administrator 5502 can be located at the server as described above. The administrator 5520 can perform configuration on the user interface at block 5504 hosted on the server, for example, configuration of the parameters of the system in FIG. 3A or other monitoring systems in other hospital rooms. The user interface 5504 may also facilitate monitoring of the system, for example monitoring the cameras and processors connected to the server.

After performing the system configuration, the administrator 5502 can update the system configuration in the database (such as the database described above) at block 5506. As described above, the system can receive the configuration information from the database 5506. Configuring the system may include calibrating the cameras, configuring the cameras and/or the processors with the configuration parameters. The server may configure the system. Configuration may be done upon initial startup of the system.

With continued reference to the example process 5500 show in FIG. 5, a person 5508 entering the field of view of the camera is detected at block 5528. The raw image frames of the camera are processed locally on the processor of the camera as described herein. The processors of the imager can extract coordinates and activity features of the detected person from the frame captured by the associated camera. The processors of the imager can update the track associated with the detected person at block 5510.

The status of the track associated with the detected person may change depending on activities taken by person and/or location of the person etc. As will be described in more detail below, the processors of the imagers can assume that any person in the room must have entered via the designated entrance/exit and can only leave the room through the same designated entrance/exit. In the example process 5500, if the detected person's track was previously present (which confirms the person' presence in the room prior to the particular frame that is being analyzed) and the person is close to the entrance/exit, the processor of the imager can delete the track at block 5512. The person is assumed to be leaving the room. If the person is close to an entrance but the person's track was not present in a previous frame, the processor creates a new track with an automatic contaminated status at block 5514. The processor of the imager may assume that any person who has just entered the room should be considered tainted or contaminated. This assumption can improve patient safety. If the person remains near the entrance, the processor may confirm the person's new track at block 5526. This person is assumed to stay in the room rather than making a temporary visit to the room before exiting the room, for example, someone who realized he or she has entered the wrong hospital room. If the person is in a location other than near the entrance/exit, the processor of the imager may also confirm the person's track at block 5526. The processor of the imager may implement additional logic as described herein (for example, under the heading "Example Tracking Logic to Reduce Errors") to determine actions to be taken on tracks, such as creating, deleting, and updating the tracks of any person detected in an image frame of the associated camera.

A detected person may become occluded from the view of a camera, for example, by another person in the room or if the detected person is hiding behind an object in the room. The processor of the imager may resolve occlusions by exchanging information between processor(s) of one or more other imagers of the system at block 5524. The processor of the imager may confirm a track and/or track state based at least in part on the exchange of information with processor(s) of the other imager(s) in the room. Additional details for resolving errors caused by occlusions are described further below (for example, under the heading "Matching Between Cameras").

As described above, initially anyone entering the room is automatically assigned a contaminated status by the processor of at least one of the imagers. With continued reference to the example process 5500, the processor of one of the imagers can update a detected person's status to clean at block 5516 if the person is close to a handwashing station, such as a sink or hand sanitizing station and has complied with a hand hygiene protocol as determined by the system. If the person approaches the sink or sanitizer location, the micro actions forming the activity features are parsed through a Markov Chain for the processor of the imager to determine if the person has washed or sanitized his or her hands. The CNN structure running on the processor of the imager can receive camera input to extract features related to hand washing or sanitizing. The camera input can include a plurality of image frames in sequence. For example, for a 10 second duration at about 30 frames per second, the camera input that is related to a person's activity can include about 300 frames in sequential order. The CNN can extract features related to hand washing or sanitizing from each of the frames in sequential order. The extracted features from each frame can be fed to the RNN structure. Output of the RNN structure of each image frame can be combined to output a state of whether the person has washed or not washed the hands.

If the person has washed or sanitized his or her hands, the processor of one of the imagers can reset the person's status to a clean status. Optionally, the processor may only set the person's status to clean if the appropriate sequence (or series of steps) and desired handwashing duration is satisfied. At block 5518, the processors of the imagers of the system may ignore (that is, not output an alert) a detected person with a status of clean if the detected person is close to a patient's bed, for example within a patient zone described herein. As the detected person approaches the patient's bed, the processor of the imager can calculate the distance of the detected person to the bed using the real-world coordinates from the depth camera. When the distance drops below a predefined threshold, the processor of the depth camera can evaluate the person's hand hygiene status.

If a detected person with a status of contaminated is within a patient zone, the processor of the imager generates an alert at block 5520. The alert may be an auditory and/or visual signal and may contain a message. The processor can output the alert a display device at block 5522. As described in greater detail herein, the system may include multiple display devices. The processor of the imager may determine, based at least in part on the initial configuration parameters, the display device that is nearest to the activity of interest, such as a contaminated person entering the patient zone. The processor of the imager may locally or directly output the alert to the determined nearest display. The processor of the imager may not send the alert to the server.

Figure 6A:
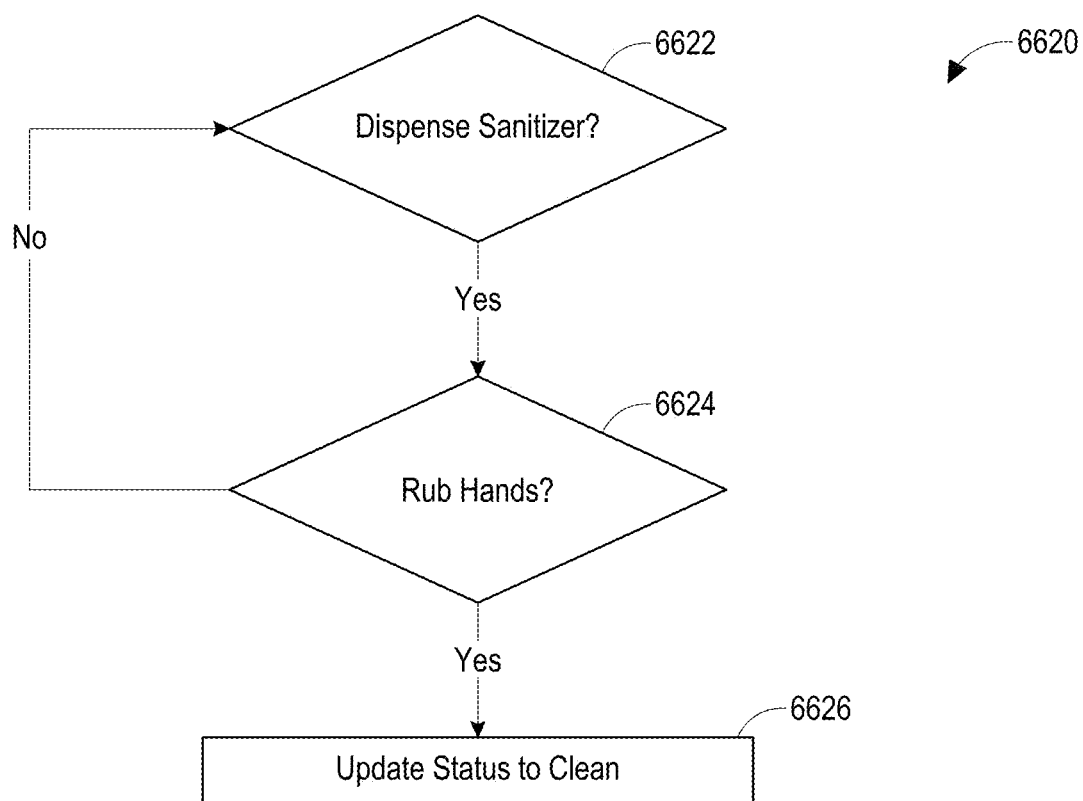
FIGS. 6A-6B illustrate example processes of hand hygiene compliance detection.
Figure 6B:
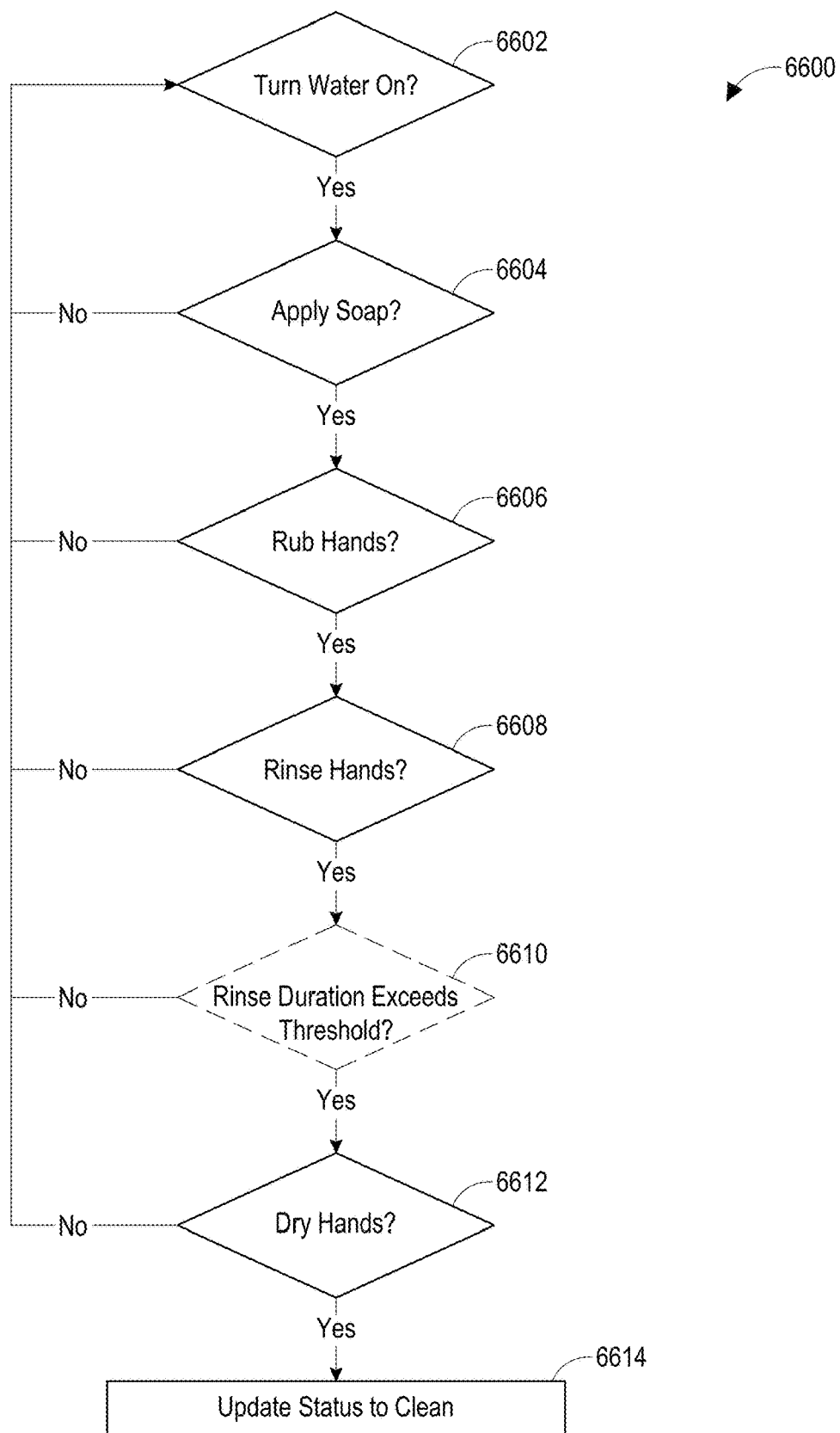

FIGS. 6A-6B illustrate example processes of hand hygiene protocols. The protocols may require the appropriate sequence and desired handwashing duration in addition to the detection of a hand sanitizing or washing micro action. As described herein, the processors of the imagers may implement one or more hand hygiene protocols. One or more cameras, such as camera 3304 in FIG. 3A, may monitor one or more handwashing or hand sanitizing stations for compliance with a hand hygiene protocol. The camera may be located above the handwashing station and may be pointed downward to view the handwashing or hand sanitizing station. For example, the camera may be located above a sink or a hand sanitizer dispenser. Based on the images received by the camera, a person's actions are parsed, for example using a Markov chain to determine whether the person has complied with the hand hygiene protocol. The processor associated with the camera that monitors the handwashing or hand sanitizing station can confirm the track of a detected person by exchanging the tracker information with other imagers. Optionally, the processors of the imagers in the room can share a database of the trackers.

The processor associated with the camera that monitors the handwashing or hand sanitizing station or a processor of another imager may determine whether the person has complied with the protocol and/or may determine the degree to which the person has complied with the protocol, for example by assigning a score to the handwashing or hand sanitizing event. That processor or a processor of another imager may output an alert if a person has not satisfied the requirements of the determined protocol and/or their compliance with the protocol has failed to meet a certain threshold. The outputted alert may warn people regarding a person with a contaminated status for example if a person with a contaminated status is too close to a patient. The outputted alert may additionally and/or alternatively provide feedback regarding a person's hand washing practices. For example, the processor may determine that a person has satisfied the hand hygiene protocol and may update their status to clean but may also provide feedback to the person about how he or she can improve handwashing or hand sanitizing in the future. Additionally and/or alternatively, the processor may output an alert while the person is washing their hands to provide feedback in real-time about how the person can improve his or her handwashing or hand sanitizing.

FIG. 6A illustrates an example hand hygiene protocol 6620 that relates to cleaning hands with hand sanitizer. At step 6622, the processor associated with the camera that monitors the handwashing or hand sanitizing station determines if a detected person has dispensed hand sanitizer. If step 6622 has been satisfied, the processor determines, at step 6624, whether the person has rubbed hands together. If step 6624 has been satisfied, the processor updates the person's status to clean at step 6626. If the hand hygiene protocol has not been satisfied, the processor maintains and/or updates the person's status to contaminated. Each step of the example hand hygiene protocol 6620 may include additional requirements. For example, the hand hygiene protocol 6620 may require that a person rub their hands together for a certain length of time at step 6624.

FIG. 6B illustrates an example hand hygiene protocol 6600 that relates to cleaning hands with soap and water. At step 6602, the processor associated with the camera that monitors the handwashing or hand sanitizing station determines whether the water of the handwashing station has been turned on. If step 6602 has been satisfied, the processor determines whether the person has applied soap to their hands at step 6604. If step 6604 has been satisfied, the processor determines whether the person has rubbed their hands together at step 6606. If step 6606 has been satisfied, the processor determines whether the person has rinsed their hands at step 6608. If step 6608 has been satisfied, the processor determines if the person has dried their hands at step 6612. If step 6612 has been satisfied, the processor may update the person's status to clean at step 6614. If the processor determines that any of the steps above have not been satisfied, the processor maintains and/or updates the person's status to contaminated.

In some embodiments, the hand hygiene protocol 6600 may include additional steps. For example, the processor may perform an additional step 6610 to determine whether the person has rinsed their hands for longer than a determined threshold after step 6608 has been satisfied. The threshold may be any length of time and may vary depending on other factors such as type of soap used. For example, the threshold may be about at least nine seconds for antiseptic soap and/or may be about at least 20 seconds for regular soap. If the person fails to satisfy step 6610 by failing to rinse for longer than the determined threshold, the system may maintain the person's status as contaminated. If the person has satisfied the requirements of step 6610 by rinsing for longer than the determined threshold, the system may continue to determine satisfaction of subsequent steps in the protocol as described above.

In some embodiments, the steps of the hand hygiene protocol 6600 may include additional requirements. For example, one or more other steps of the protocol 6600 may require that a person perform the action of the step for a certain length of time to satisfy the requirements of that step.

Example People Recognition/Tracking Tools

Figure 8A:
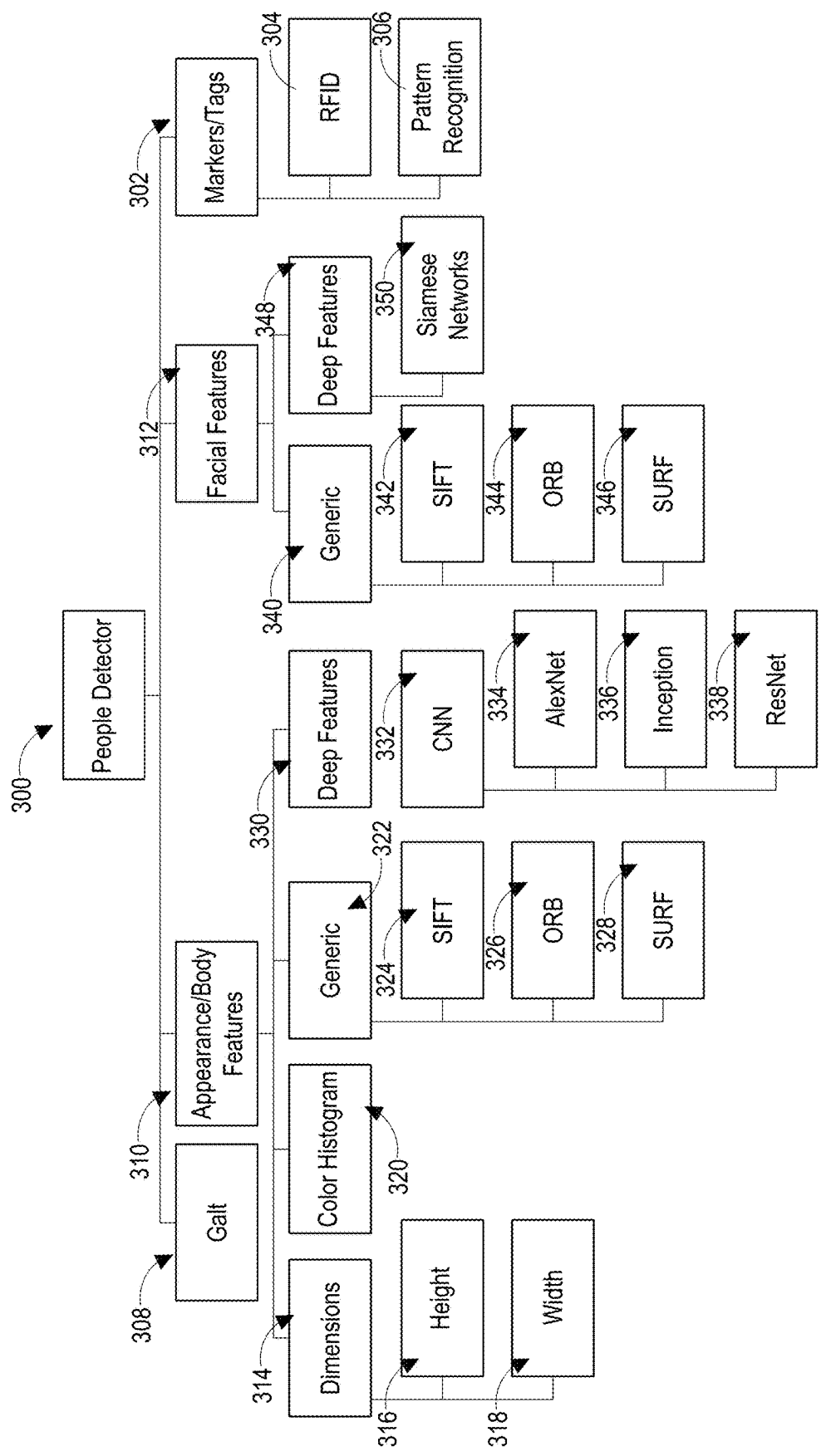
FIG. 8A illustrates an example people detecting module and parameters monitored by the people detecting module.

Additional details of the people detector module are shown in FIG. 8A. As shown, the people detector module can detect people using a movement module (such as gait module 308), an appearance and/or body features module 310, and/or a facial features module 312. The people detector module 300 can also detect people by ID markers and/or tags 302, such as RFID tags 304 and/or a pattern recognition module 306. The people detector module 300 can, combine detection by markers and/or tags 302, with detection of gait 308, appearance and/or body features 341, and/or facial features 312.

Figure 8B:
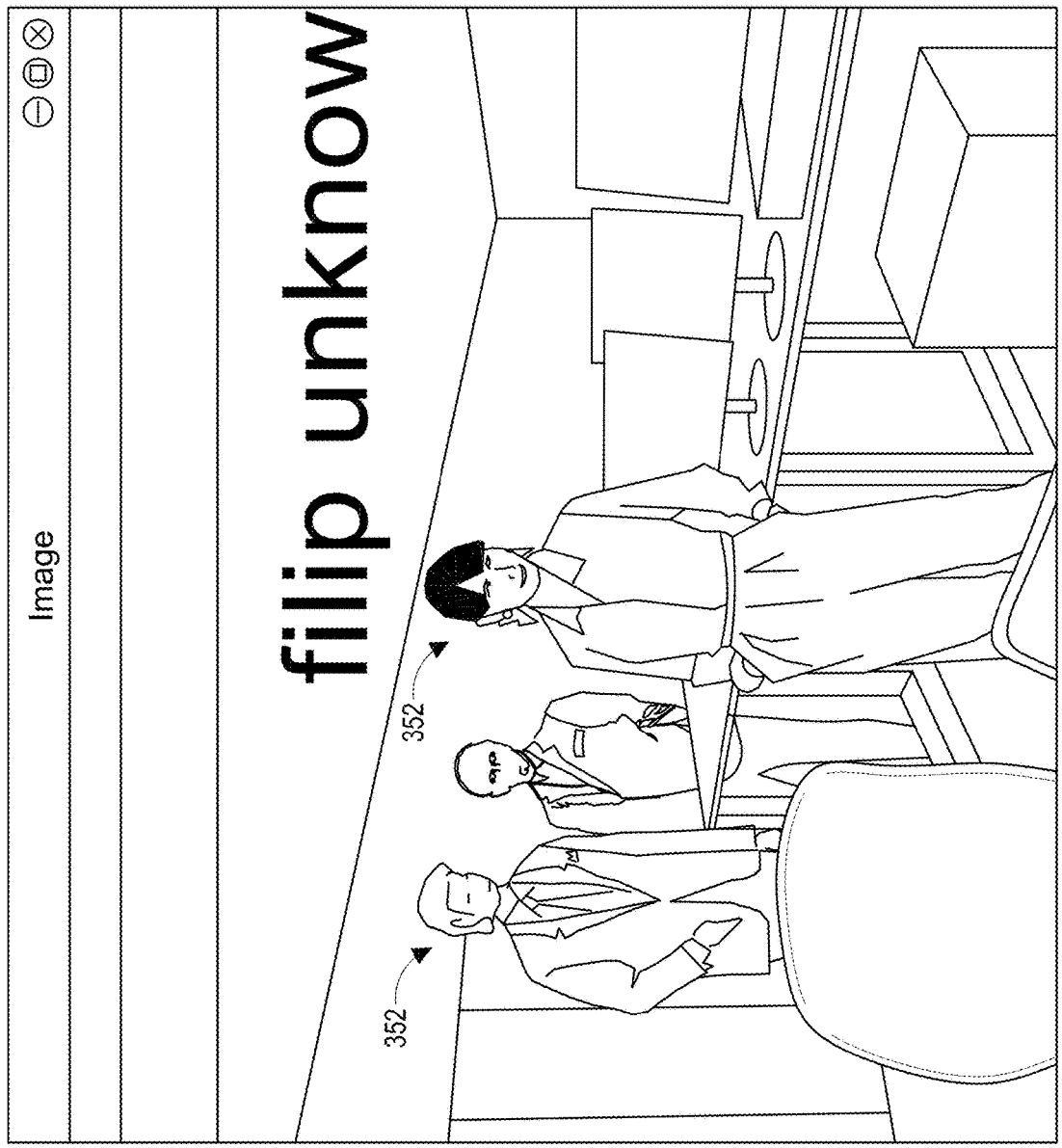
FIG. 8B illustrates an example camera image with identification information of people using a face recognition module displayed in the image.

The people detector module 300 can use a plurality of computer vision toolboxes. For example, a computer vision toolbox can be used to draw a boundary around the person's face 352, such as shown in FIG. 8B, or around the person's body, such as shown in FIGS. 13A-13D. As shown in FIG. 8A, the appearance and/or body features module 310 can include algorithms for determining dimensions 314 (such as height 316, weight 318, and/or otherwise), color histogram 320, and generic algorithms 322 (including but not limited to the scale-invariant feature transform (SIFT) algorithm 324, the Oriented FAST and Rotated BRIEF (ORB) algorithm 326, the speeded up robust features (SURF) algorithm 328). The appearance and/or body features module 310 can also include deep learning features 330, such as the convolutional neural network (CNN) 332, which in turn can include the AlexNet 334, the Inception 336, and/or the ResNet 338.

Example Facial Recognition Module

As shown in FIG. 8A, the facial features module 312 can include generic algorithms 340, including but not limited to the SIFT algorithm 342, the ORB algorithm 344, the SURF algorithm 346. The facial features module 312 can also include deep learning features 348, such as the Siamese Networks 350 and/or otherwise.

The face recognition module, such as Google's Facenet, can store 512 vector numbers that can uniquely identify a known person's face. As shown in FIG. 8B, such a face recognition module can send extracted facial features to the server, which can output the person's name. In this disclosure, the boundary boxes, numbers, and/or names illustrated as being displayed in a camera image are used to illustrate the functions of the clinical activity monitoring system. Such images, such as the images shown in FIGS. 8B, 11, 13A-13D, and 14A-14B, may not be displayed anywhere in the system. The 512 vector numbers can encompass facial features corresponding to points on ones' face. Facial features of known people (for example, clinicians and/or the like), can be stored in a facial features database, which can be part of the database described above. To identify an unknown individual, such as a new patient or a visitor, the face recognition module can initially mark the unknown person as unknown (see FIG. 8B) and subsequently identify the same person in multiple camera images. The face recognition module can take multiple measurements in each image and populate the database on the central server dynamically with the facial features of the new person. The system can include a deep learning network structure such as described above and shown in FIG. 8A to learn and adapt at the same time based on the identification of the unknown person.

Color Marker Identification

As described above, the system can include an identification tag that can include a visual marker to supplement the face recognition module in identifying people. The identification tag can also optionally be used for identifying objects.

Visual marker systems typically can have a set of patterns that can be detected by a computer equipped with a camera and an appropriate detection algorithm. Typically markers are placed in the environment or on objects to enable a computer to easily detect and identify points on interest in the real-world or to compactly represent some information. Markers that are designed explicitly to encode information usually work at short and/or fixed distances from the camera, for example, QuickResponse (QR) codes, MaxiCode, etc. In contrast, markers that are designed to identify points of interest are expected to work at larger distances. The markers disclosed herein can be detected and decoded in both the short and longer distances, in the presence of orientation variations, translation, sheer, illumination and other variances, partial occlusions, and/or the like.

A large number of existing marker systems utilize a unique pattern of black and white pixels, which may be difficult to detect by the camera due to variance in the lighting conditions. The present disclosure provides an example multi-colored marker system to generate and read unique color patterns such as the pattern 500 shown at the bottom of an example identification tag 504 in FIG. 9B. The colors used in the system can be invariant and/or less susceptible to lighting conditions, for example, by being a predetermined distance from each other in a color spectrum. For example, the colors can be from a CMY (Cyan, Magenta, Yellow) color model, a CMYK model (Cyan, Magenta, Yellow, Black), or an RBG (Red, Blue, Green) color model. The number of cells can be varied. There can be a minimum of three cells. In some configurations, the marker can have six cells (excluding the header and last cells). More than one cell in the marker can use the same color. In some configurations, adjacent cells of the marker cannot be of the same color so that it is easier for the processor to detect the borders of the individual cells.

Figure 9B:
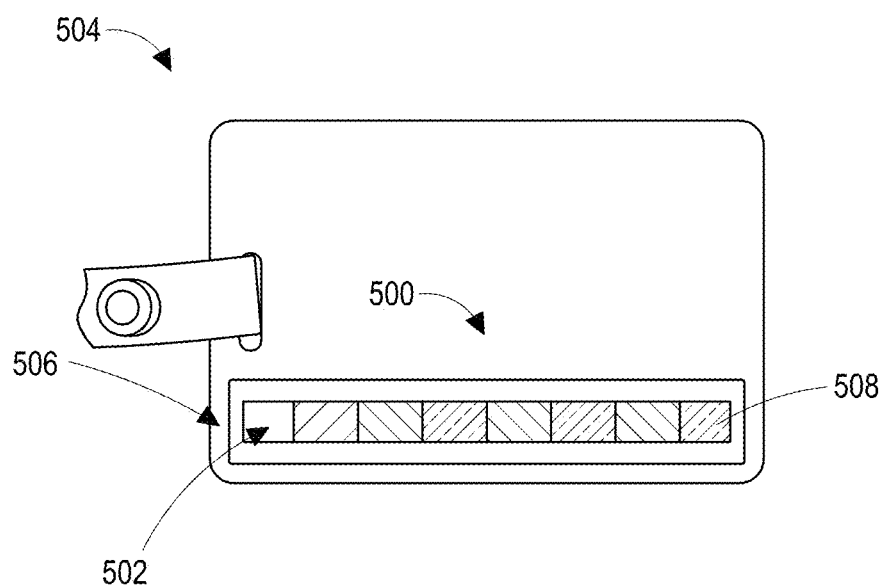
FIG. 9B illustrates an example identification tag with an example color-coded marker for use in an example clinical activities monitoring system.

As shown in FIG. 9B, the multi-colored marker can include a unique pattern (for example, a sequence) of colors 500. The marker can be located on an ID tag 504, for example, along an edge of the tag or at any other locations on the tag. The unique pattern of colors 500 can map onto an identification number associated with the person and/or object on which the tag 504 is worn. The marker 500 can be used to uniquely identify people walking through an environment with the marker 500 visible to cameras (such as the high-resolution cameras 400 in FIG. 9A or the cameras shown in FIGS. 1A, 1B, 2A, and 2B) mounted at various distances and angles within that environment, for example, a room, walkway, hospital ward, and the like. The marker can have a dimension such as the marker can be detected and analyzed by the cameras disclosed herein from a distance greater than allowed by QR code, RFID code, and the like.

As will be described in greater detail below, the identification algorithm based on the pattern 500 can allow the pattern 500 to be detected and analyzed without requiring the tag 504 to be directly facing the camera at a particular angle or oriented in a certain way. The pattern 500 can be detected and analyzed, for example, when the tag 504 is slanted relative to the camera lens, and/or worn upside down. In some examples, the pattern 500 can be printed on both sides of the tag 504 so that the camera can detect the pattern 500 regardless of which side of the tag 504 is facing outward from the person wearing the tag 504 or from the object on which the tag is placed.

Figure 10:
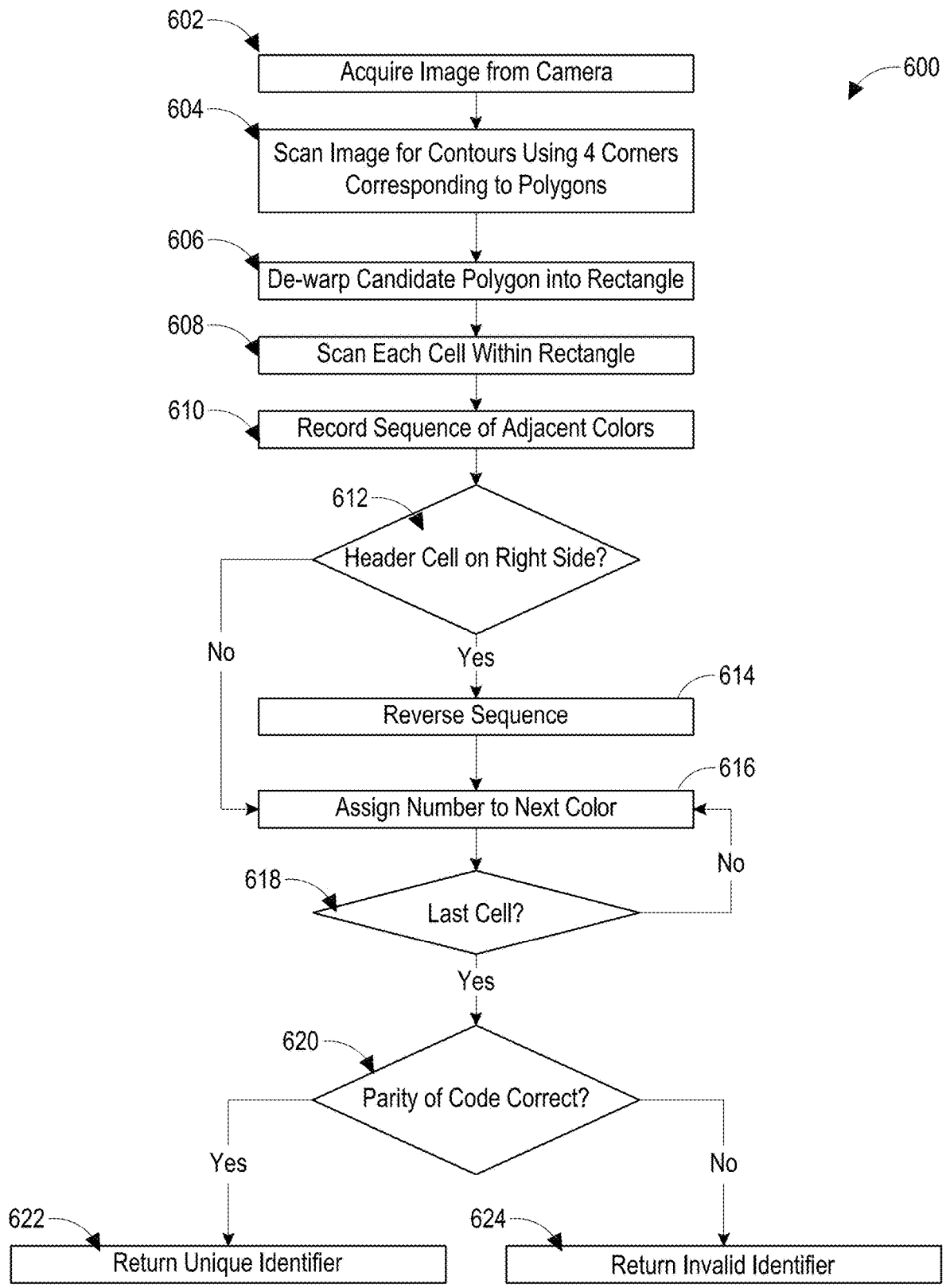
FIG. 10 illustrates an example process of using an identification tag with a color-coded marker.
Figure 11:
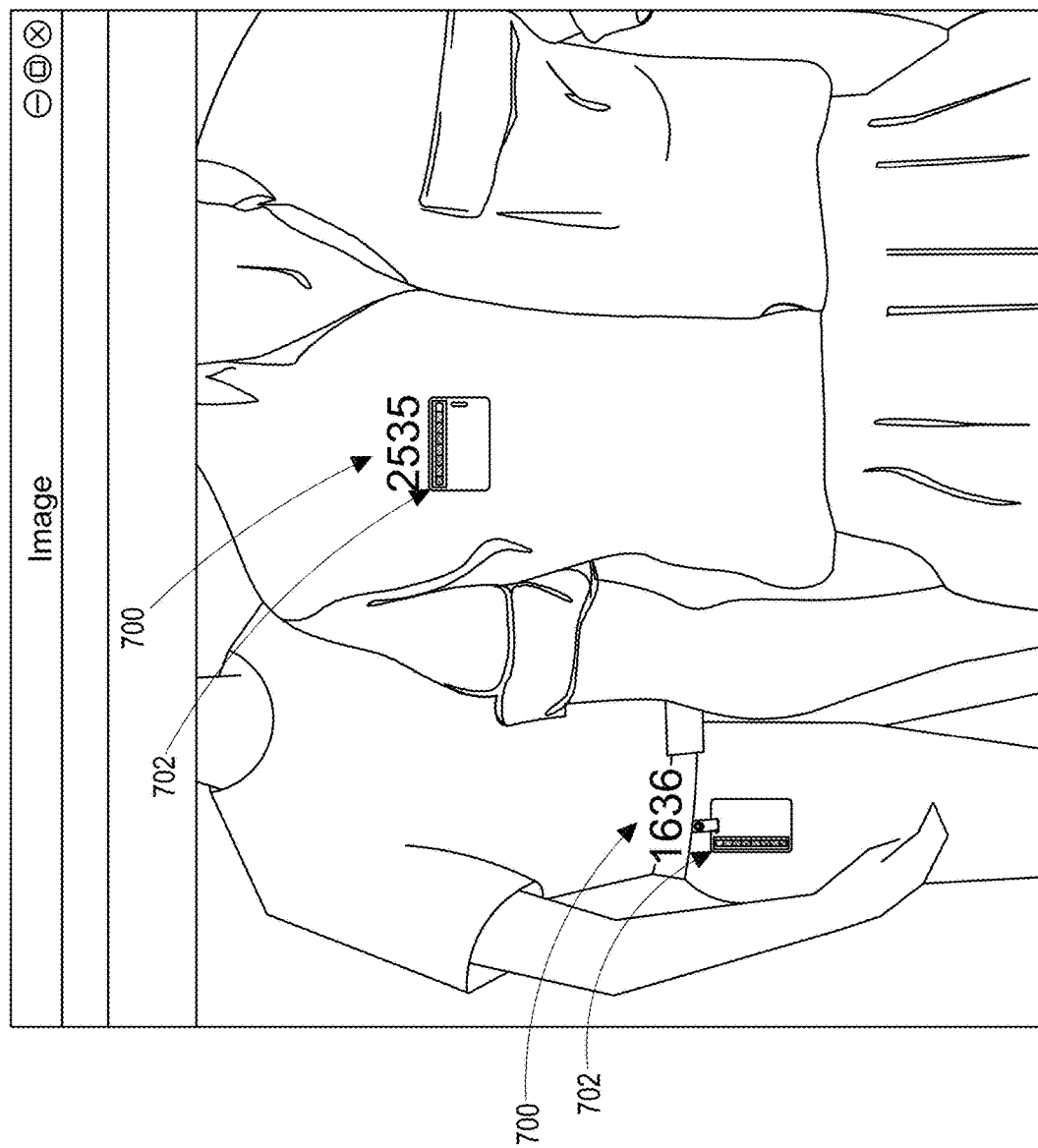
FIG. 11 illustrates an example camera image with unique identification numbers of color-coded markers displayed in the image.

FIG. 10 illustrates an example detection algorithm 600 using the unique pattern of colors (such as the pattern 500 in FIG. 9B). At step 602, a processor of a high-resolution camera can acquire an image or frame from the high-resolution camera. At step 604, the processor can scan the image for contours with four corners corresponding to polygons. In some configurations, such as shown in FIG. 9B, the sequence of colors can be enclosed by a border 506 having a different color than the sequence of colors (such as a black border). The border 506 can aid in identifying the marker 500. At step 606, the processor can de-warp each candidate polygon into a rectangle to adjust the orientation and sheer of the candidate polygon. Example rectangles 702 are illustrated in FIG. 11. The rectangles 702 may not be displayed anywhere in the clinical activities monitoring system. At step 608, the processor can scan each cell within the rectangle to detect the color in each cell. At step 610, the processor can record the sequence of adjacent colors.

At decision block 612, the processor can determine whether the header cell is on a right hand side of the image. The header cell can have a predetermined color and/or dimension. The header cell can be identical in each marker. The header cell can have a color that is not used for the remaining sequence of colors. For example, as shown in FIG. 9B, the header cell 502 can be white. If the header is on the right hand side of the image, the processor can reverse the sequence of colors at step 614 as the tag on which the marker is located is worn upside down. At step 616, the processor can assign a unique number to each next color. When mapping each color to a number, the processor can also optionally weigh the color (except for the header cell and the last cell) based on its position and determine based on the weighted numbers (for example, by summing the weighted numbers) a unique identifier number. The number of available colors (for example, about 3 or 4 different colors as described above) and the number of cells (for example, six cells, excluding the header cell and the last cell, as shown in FIG. 9B) in each marker can provide hundreds, thousands, or more, unique identifier numbers.

At decision block 618, the processor can determine whether the next color is the last cell. The last cell 508 (FIG. 9B) can have a different dimension (for example, being shorter or longer) than the cells between the header cell 502 and the last cell 508. Additionally and/or alternatively, the last cell can have a color that is different than the rest of the cells between the header cell 502 and the last cell 508. If the next color is not the last cell, the processor can return to step 616. If the next color is the last cell, the processor can determine the color of the last cell, which can indicate the parity of the entire code. One color can indicate that the number of cells should be even. Another color can indicate that the number of cells should be odd. At decision block 620, the processor can determine whether the total number of cells follow the parity code as indicated by the color of the last cell.

If the parity of the code is consistent with the color of the last cell, the processer can output the unique identifier number at step 622. Example unique identifier numbers 700 are illustrated in FIG. 11. The unique identifier numbers 700 may not be displayed anywhere in the clinical activities monitoring system. If the parity of the code is not consistent with the color of the last cell, the processor can return an invalid identifier message. Accordingly, the pattern 500 includes error correction mechanisms, such as the border 506, the header cell 502, and the last cell 508 disclosed herein.

If multiple people and/or object with an identification tag disclosed herein are in the field of view of the camera, the multiple markers can be processed substantially simultaneously (see FIG. 11). The unique identifier number can be associated with an identification of the person and/or object. After the processor has determined the unique identifier number of a detected marker, the processor can look up a database (such as the database of the server) storing the pairing of the unique identifier number and the associated person or object, and output the name and/or other identifying information about the person or object. The database can store pairs of the unique identifier number and the people and/or objects that are expected to be present at the clinical setting more regularly, for example, a clinician, a hospitalized patient or a patient who visits the clinical setting routinely. Before a new person (for example, a visitor) and/or an object enters the clinical facility, a tag with a new multi-colored marker can be issued to the new person and/or object. The database can also store pairing of the new person and/or object (for example, in a temporary folder). A single detection based on the multi-colored marker can be sufficient for accurately tracking the person and/or object in subsequent images of the same and/or different cameras.

The shape of the cell in the pattern can be varied, for example, in the form of a square, a rectangle, a triangle, a circle, or otherwise. The pattern of colors does not necessarily need to be in one row or column. The pattern of colors can also alternatively be in more than one row and/or column (for example, as a matrix, a grid, a circle, and/or otherwise).

Motion Tracking Module

Figure 12:
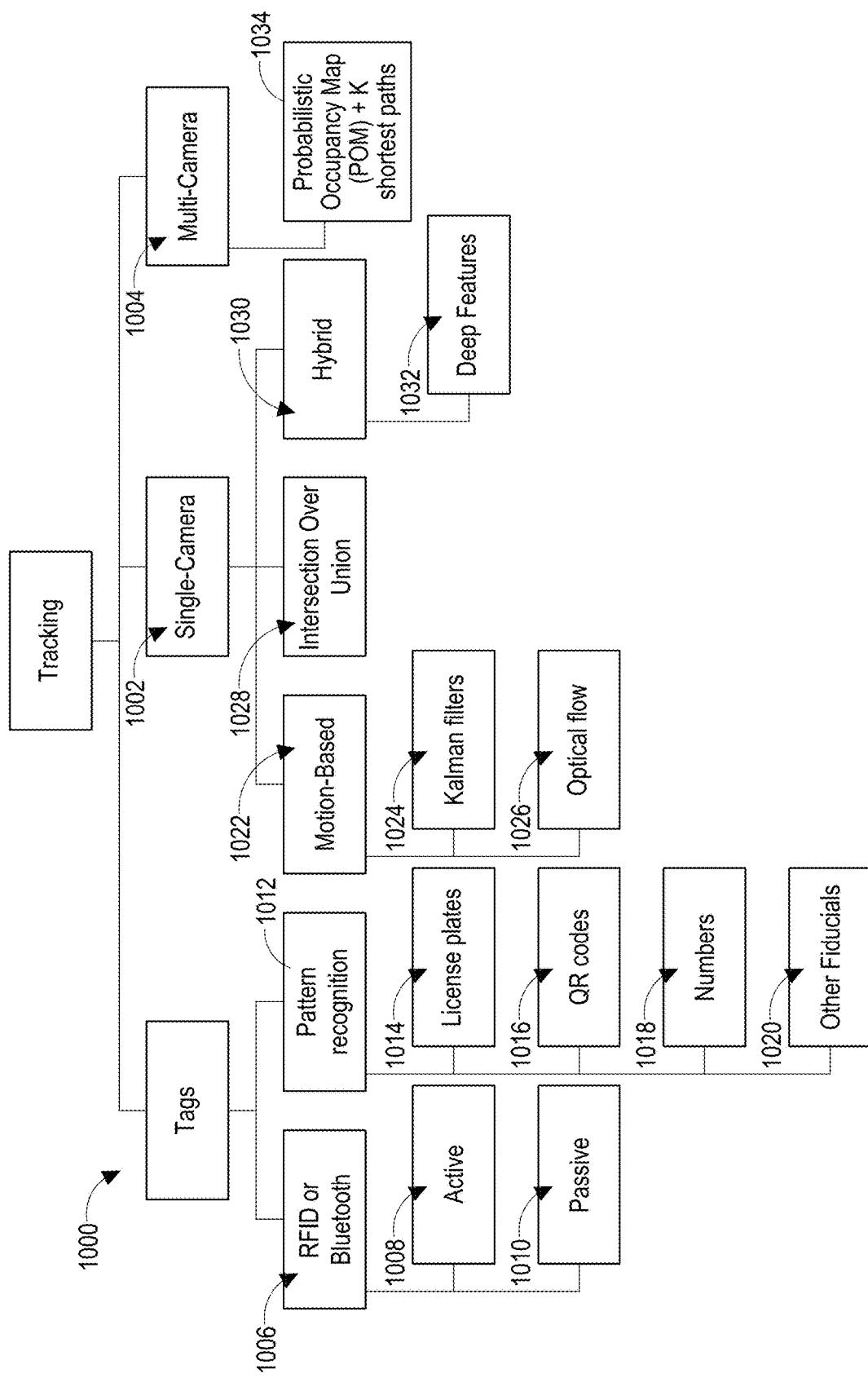
FIG. 12 illustrates an example tracking module and parameters monitored by the tracking module.

FIG. 12 summarizes example tracking functions performed by the system disclosed herein. As described above, the tracking can be performed using the identification tags 1000, the single camera tracking module 1002, and the multi-camera tracking system 1004. The identification tags 1000 can include RFID tags 1006 (which can be active 1008 and/or passive 1010) or Bluetooth or BLE tags 1006. The identification tags 1000 can also include pattern recognition functions 1012, for example, by recognizing license plates 1014, QR codes 1016, numbers 1018, the pattern of colors, and/or other fiducial markers 1020. The single camera tracking module 1002 can provide motion-based tracking 1022, for example, using Kalman filters 1024, optical flow based motion detection 1026, and/or others. The single camera tracking module 1002 can perform an intersection over union calculation 1028. The single camera tracking module 1002 can also include a hybrid deep learning architecture 1030, for example, with a module for extracting deep learning features 1032. The multi-camera tracking system 1004 can output a probabilistic occupancy map (POM) and calculate the K shortest paths 1034 so as to track the same person across images of different cameras at the same scene.

The processors on the cameras disclosed herein can include a people tracking module. FIGS. 13A-13D illustrates example screenshots of the camera images. Outputs of the people tracking module are shown as being superimposed over the images for illustration purposes. Neither the camera images nor the outputs may be displayed anywhere in the clinical activities monitoring system. As described above, the cameras may only transfer the outputs of the tracking modules or otherwise post-processed data to the central server, without sending the actual images of the clinical setting. When the individual tracking module identifies a person, for example, using the toolboxes disclosed herein, the module can place a border or a virtual box around the person. As shown in FIGS. 13A-13D, the border can be rectangular in shape. The border can have any other shape, for example, in the form of an ellipse, a silhouette of the detected person, or otherwise.

Figure 13A:
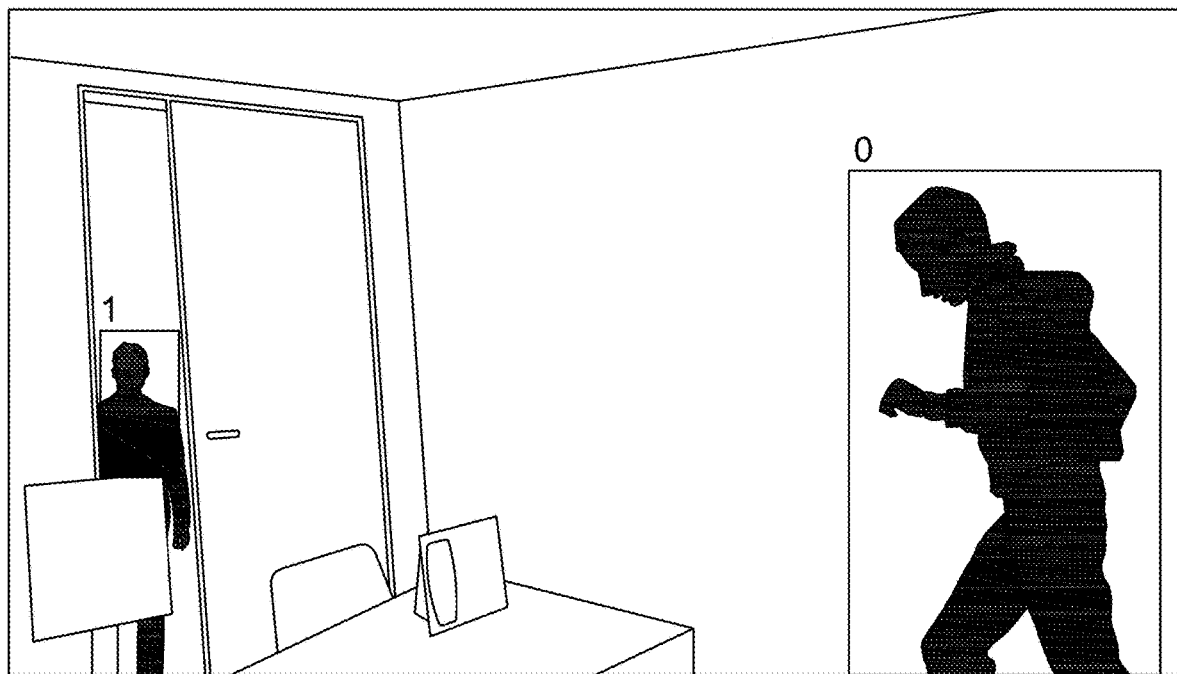
FIGS. 13A-13D illustrate example camera images with tracking of individuals displayed in the images.
Figure 13B:
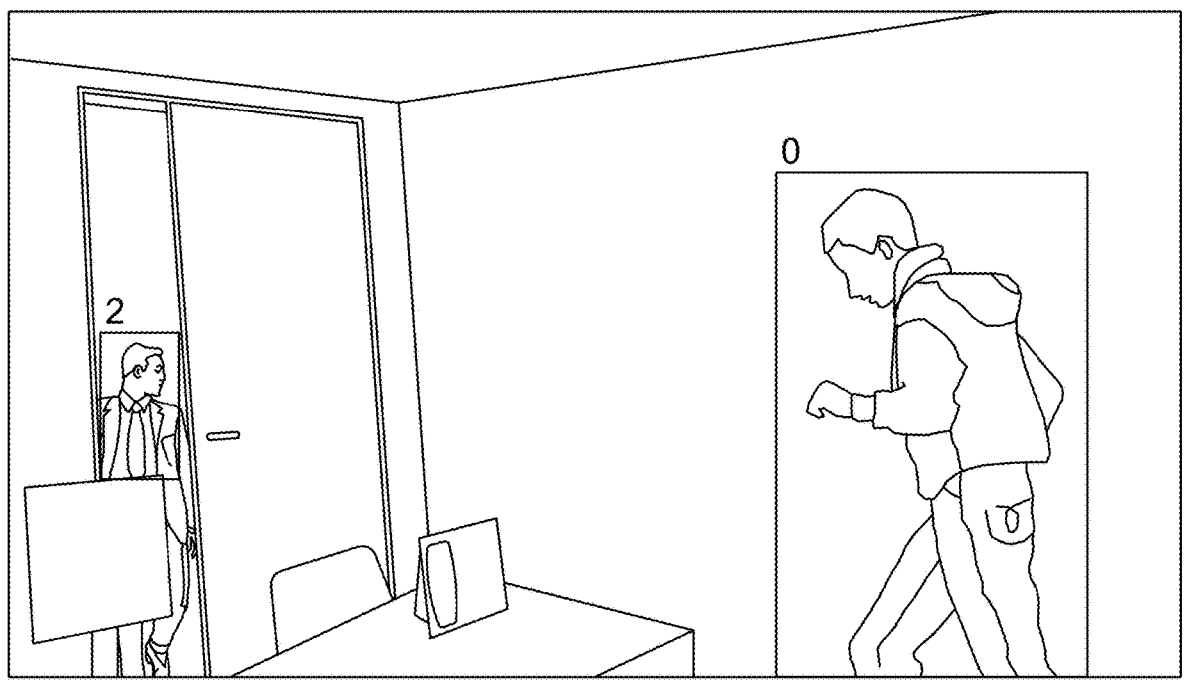
Figure 13C:
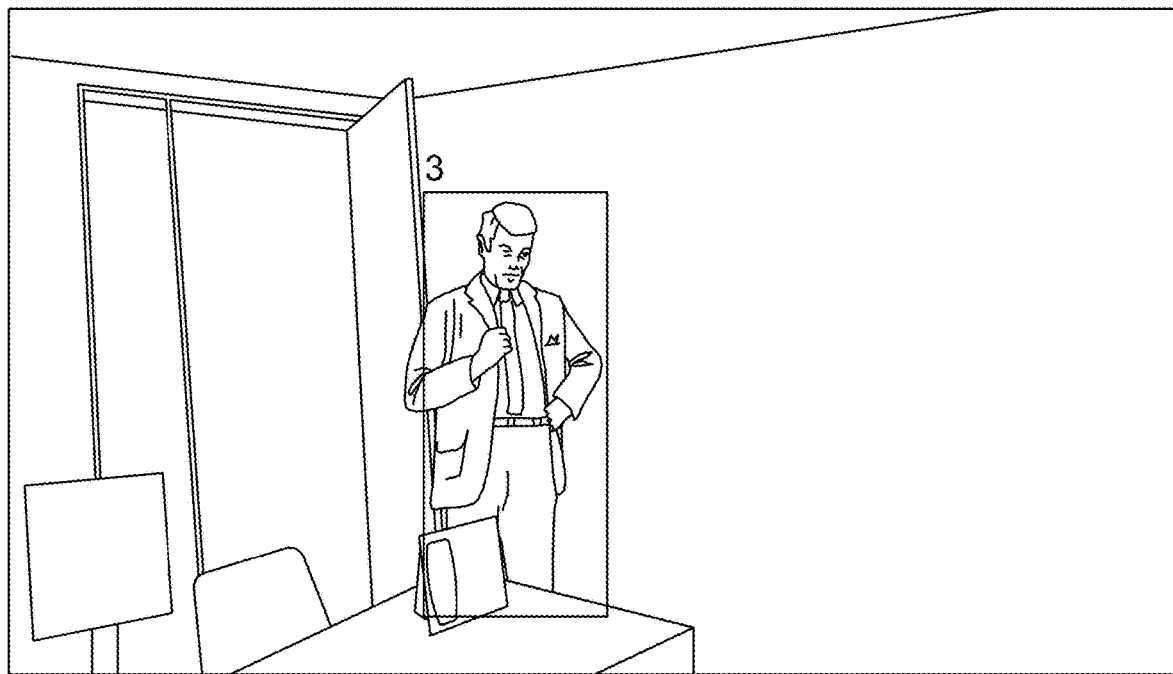
Figure 13D:
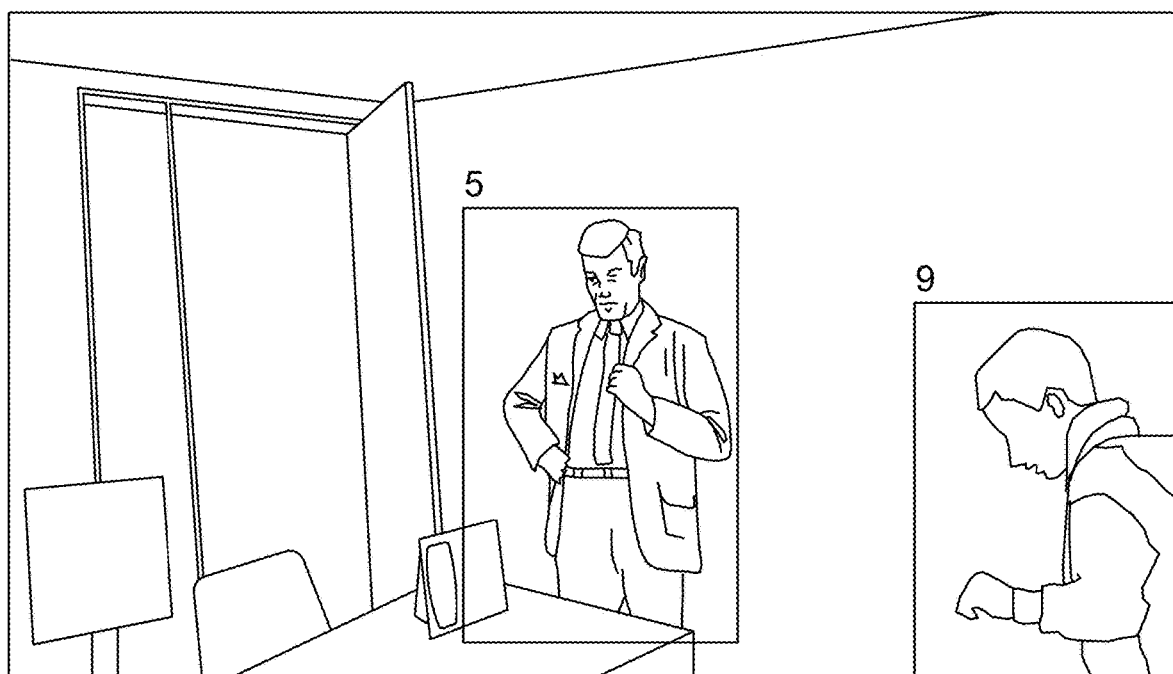
Figure 14A:
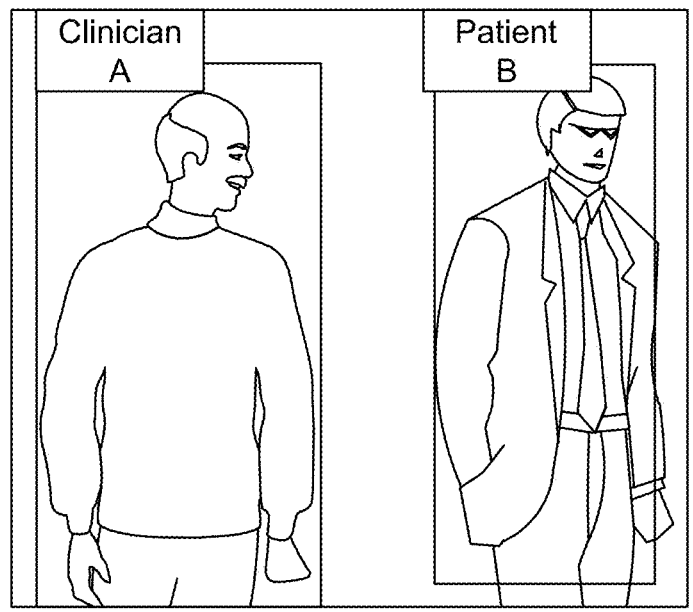
FIGS. 14A and 14B illustrate example camera images from different cameras with tracking and identification of individuals displayed in the images.

The module can be configured to identify a person in rooms with low lighting, such as shown in FIG. 13A. The module can be configured to track the same person after the person has been temporarily occluded and therefore not visible in the camera image. As shown by comparing FIGS. 13B and 13C, the same person can be assigned a different number (No. 2 in FIG. 13B versus No. 3 in FIG. 13C after the same individual has walked into a room in which the camera is located through a door). Similarly, when the person No. 0 in FIGS. 13A-13B moved outside the field of view of the camera in FIG. 13C and returned into the field of view in FIG. 13D, the same person can be reassigned a new number, No. 9. That is, the people tracking module may optionally tracking a person without identifying the person. This can reduce the processing power requirement for implementing the people tracking module. The output of the people tracking module on one camera in the room can be combined with the output of the face recognition module and/or the output of the identification tag detection run by the processor of the same camera or a processor of a second camera in the same room, such as shown in FIG. 14A, in which the persons, Clinician A and Patient B, can be identified and the border surrounding Clinician A and Patient B can follow Clinician A and Patient B's movements to track the whereabouts of the Clinician A and Patient B. Having different modules run by processors of different cameras can facilitate having all image processing performed by the processors of the cameras.

Example Multi-Camera Tracking Features

Figure 14B:
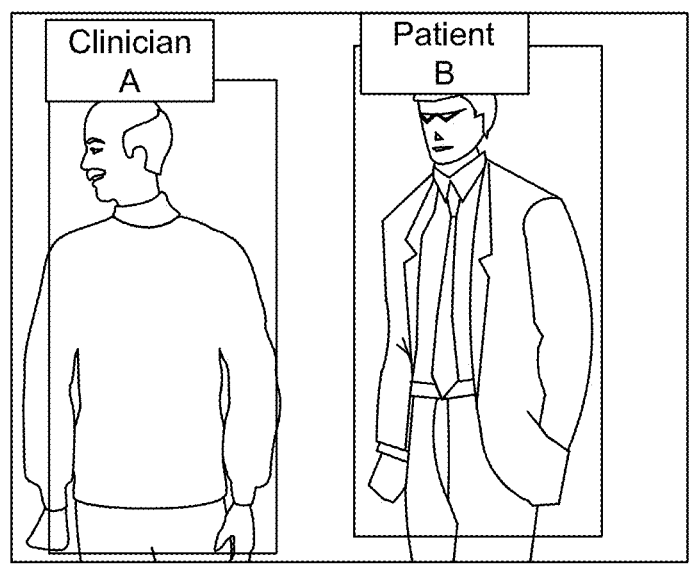

As shown in FIGS. 14A-14B, the system can also identify and track people, as illustrated by Clinician A and Patient B, across different cameras that are at different locations of the same scene, for example, within the same room.

To accommodate the processing capacity of the processors on the cameras, some detection and/or tracking module(s) can be performed on one camera, and other some detection and/or tracking module(s) can be performed on another camera at the same scene. For example, the processor on one camera can run the face recognition module and/or other people detection modules, and the processor on another camera can run the marker detection module.

The more than two different cameras can be located anywhere in the scene, for example, as shown in FIGS. 2A and 2B. As the cameras are not configured to move and the background (for example, including the stationary objects such as the hospital beds, handwashing stations, etc.) is substantially fixed, the difference from key points in one camera and the other camera(s) can be preserved. The accuracy of the cross-camera mapping can be improved with distances calculated from multiple fixed reference points in the scene shared between the cameras The system can include at least two or more (for example, four, six, or otherwise) cameras in the same scene. Processors on the cameras in the same scene can process the virtual or boundary boxes to perform activity monitoring, for example, whether a person at the same scene has washed his or her hands before entering a patient zone.

The server can receive coordinates of the virtual box or boundary box without receiving the background or raw motion information. All the image processing can be performed by the combination of the processors on the cameras at the scene. This can reduce the amount of bandwidth required to transmit information to the server, for example, resulting in orders of magnitude less of bytes being transmitted. As no images are sent, confidentiality and/or privacy at the clinical setting can be better preserved.

Example Tracking Logic to Reduce Errors

The processors of the imagers can implement various logics to improve accuracy in tracking people in an enclosed hospital room, particularly when the people's identify or facial features are not available.

As described above, the tracker module of the imager may compare the intersection over union of all boundary boxes in consecutive frames. The tracking module may associate boundary boxes with a given track (that is, the sequence of boundary boxes associated with a person through consecutive frames) if the boundary boxes of consecutive frames overlap by a predetermined threshold. If the boxes in consecutive frames overlap by at least the predetermined threshold, the tracker module can assume the two boxes belong to the same person. The tracker module may assume a threshold walking or running speed of a person. A cost matrix is associated with the intersection over union calculation as a person can only move in three dimensions, which can be captured by the two-dimensional RGB camera with the depth detection.

The detection and/or tracker module(s) may create a track under one or more conditions. For example, the module(s) may create a track upon detection of a person at an entrance as described above. The entrance may be predesignated. Additionally and/or alternatively, the module(s) may create a track upon detection of a person anywhere in the room. The module(s) may require detection of a person for varying amounts of time and/or in varying numbers of consecutive image frames depending on the location of the detected person before creating a track. For example, the module(s) may require detection of a person for a longer period of time and/or in a greater number of consecutive image frames if detected in a non-entrance location of the room than if detected near the entrance before creating a track. This may ensure that a track is not created for the false detection of a person.

A track may become lost meaning the track may become disassociated from a detected person. This may occur for a number of reasons, including but not limited to occlusions, fast motion and the like. When a track is lost, the module(s) may assign the lost track a status of lost and/or assign the lost track to a pool of lost tracks such as a missing pool. The module(s) may assign any new tracks that are created in a non-entrance location of the room to a track in the missing pool. Additionally and/or alternatively, when a track becomes lost, the module(s) may search for detected persons to which it may associate the lost track. The module(s) may search for detections within a certain radius of the lost track. The size of the radius may be proportionate to the amount of time and/or number of frames for which the track has been lost, for example, based on an assumed speed limit of walking or running by an average person.

The module(s) may create a new candidate track when the likelihood of matching an existing track to a detected person is low. The module(s) may delete tracks under a number of circumstances. For example, the module(s) may delete a track when the track has been lost for a certain amount of time or if the track is near an exit region (as described above).

The module(s) may associate a detected person with an existing track. The association may be based on criteria including but not limited to the amount of overlap between the detection and the position of the track, for example the last known position of the track using two-dimensional RGB coordinates and/or depth as a third dimension. The depth information can allow the processor to determine which person is in the front and which person in the back of the room in an image frame. The criteria for associating a detected person with an existing track may include features identifying similarities such as the color of clothes, height of the person, etc.

The detection and/or tracking module(s) may use a one-shot Deep Learning network to detect people, heads and/or hands in every frame captured by the one or more cameras. Heads and/or hands that appear to be human heads and/or hands but are not contained within a boundary box or within a predefined proximity to a person's boundary box may be ignored. Heads and/or hands that are not within a boundary box and/or outside of a predefined proximity to a boundary box may be a false detection such as a mannequin or a chair. Furthermore, the detection and/or tracking module(s) may have predefined limits on the size of human body parts such as a human head or human hands. The module(s) may have predefined limits on the size of boundary boxes. The limits of the size of human body parts may be relative to the size of the boundary box. The limits of human body parts and/or the size of the boundary box may be relative to the distance from the measured object (such as the human head or boundary box) to the depth camera. For example, any object resembling a human body part, such as a toy doll or a painting may be ignored if the size of the body part is too large or too small.

The detection and/or tracker module(s) may measure the distance from a person to other objects, such as other people, the camera and the like, by measuring the distance to the person's head. To measure the distance to a person's head, the module(s) may average the distance to pixels detected on the person's head. Because the camera may be mounted at or above the level of a person's head, averaging the distance to pixels detected on the head to measure distance to the person may reduce the occurrence of occlusions.

The detection and/or tracker module(s) may track the transition of a person to different orientations relative to the camera. For example, the module(s) may track a person's transition from standing to lying down or vice versa. The module(s) may use a perspective transform algorithm to track a person's transitions. Tracking transitions may be based on a pre-determined orientation of the bed with respect to the camera.

The cameras may capture images at a high frame rate. For example, the frame rate can be at least about 7 frames per second (FPS), or at least about 10 FPS, or at least about 20 FPS, or at least about 30 FPS, or at least about 60 FPS, or more. The higher frame rate can make the intersection over union calculation of all boundary boxes more accurate. It should be understood that the cameras may capture images at a consistent frame rate, at least for known periods of time. Therefore, a period of time may be converted to a number of consecutive image frames captured within that period of time and vice versa. Therefore, as discussed herein, any reference to a period of time, for example by use of the module(s), may be converted to a number of consecutive image frames captured within that period of time and vice versa.

The module(s) may require that a potential detection be captured in several consecutive frames and/or for a certain period of time to be considered a detection. Requiring that a possible detection be captured in several frames alone or in combination with a high frame rate, may reduce the occurrence of considering temporary artifacts to be detections. For example, when a patient gets out of their bed, an imprint of the patient may remain on the bed mattress and/or blanket. The imprint may be recognized by the module(s) as a potential detection of a person but will be ignored if the imprint does not last long (that is, is not captured in several consecutive frames).

The detection and/or tracker module(s) may use a hand detection model to detect hands. This may be used at the handwashing area and/or other regions of interest in the room. The hand detection model may be used for training and/or to validate the output of the deep learning-based hand washing action recognizer module.

The detection and/or tracker module(s) may use a mask detector which may determine whether a person is wearing a mask or not wearing a mask. Based on whether a person is wearing a mask or not, the module(s) may invoke facial recognition or body-based recognition, for example for re-identification. The module(s) may invoke body-based recognition if the person is wearing a mask and may invoke facial recognition if the person is not wearing a mask. The module(s) may also use RFID and/or BLE tags, or any other ID tags disclosed herein for re-identification.

The detection and/or tracker module(s) may ignore areas of the room and/or areas within the field of view of the camera. That is, the processor may be configured to not process certain portions of raw image frames. The areas to be ignored may be predefined locations in the room which may be based at least in part on layout information of the room provided to the processor upon initial configuration. For example, the module(s) may ignore a mirror in the room in order to ignore detecting reflections of people in the mirror. Additionally and/or alternatively, the areas to be ignored may be defined by camera settings. For example, the module(s) may ignore areas beyond a predefined depth limit of the depth cameras. For example, the processor may ignore a person within the view of the camera that is beyond a certain distance from the camera, such as a person outside of the room viewed through an open doorway or viewed through a window.

Matching Between Cameras

Because two or more cameras at the same scene are substantially fixed in position and/or orientation, the processor on one camera can match a person in that camera view with the same person in an image of a different camera at the scene. This matching can be helpful when the detected person cannot be identified using the face recognition module and/or identification tag module (for example, when being assigned a negative ID, or when the person is wearing a mask as described above).

The processor on the camera(s) or the server processor can use epipolar geometry to resolve mapping of images taken by the different cameras. For any single point in one camera image, a line can be projected from that point into an image of the other camera(s). This is because all the points in one image lie in different zones in images from the different camera(s). Accordingly, the epipolar lines around a person (for example, a virtual box or any other virtual shape) can be drawn in a first image from a first camera and the four corners from the virtual box (or different numbers of corners depending on the shape of the virtual box) can be extended into an image from the second camera. The processor on the second camera or the server processor can check how far the virtual box in its image is away from the four lines that originate from the box in the first image. The processor of the second camera or the server processor can perform the same determination on a virtual box for another person that is in the image. The processor of the second camera or the server processor can determine which virtual box fits better or has the best fit within the projected lines from the first image. The processor on the first camera or the server processor can perform the same analysis based on the image from the second camera to confirm mapping of the people in the two images. The process can be repeated if more than two cameras are present at the scene.

Figure 7A:
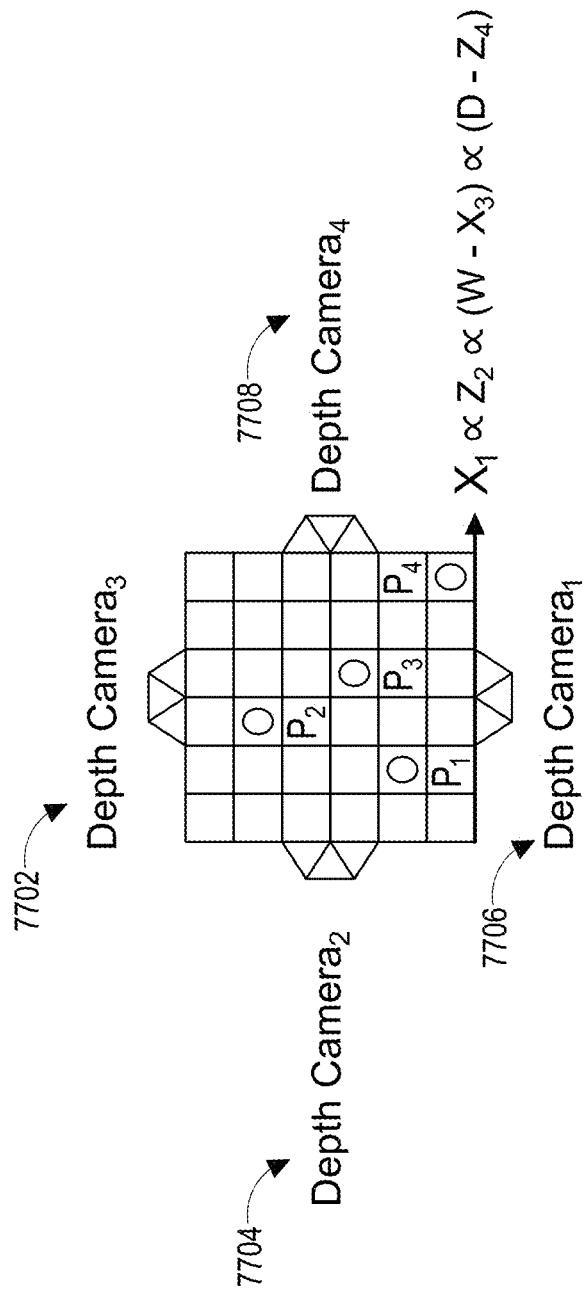
FIG. 7A illustrates schematically an example arrangement of cameras in an example clinical activities monitoring system.

FIG. 7A illustrates an arrangement of cameras in a room in an example of a clinical activities monitoring system, such as the system in FIG. 3A or any other systems disclosed herein. As shown in FIG. 7A, the example system includes four cameras (7702, 7704, 7706, 7708). The cameras may be depth cameras. The cameras are arranged to monitor the room at 90-degree angles relative to one another. The cameras may be positioned to view an entirety of the room or substantially all of the room. The cameras may track people in the room. FIG. 7A shows four people (P1-P4) in the room. Each of the cameras (7702, 7704, 7706, 7708) may independently track each person (P1-P4) in the room, for example, using a tracker module as discussed herein. The system may include a different number of cameras, such as two, three, or other number of cameras.

When multiple cameras are available in a room, the clinical activities monitoring system may use information from more than one camera to resolve errors, irregularities, mismatches and the like in the independent tracking by any one of the cameras. The errors may be caused by occlusion and/or fast motions or the like. For example, a person may be occluded from the view of one camera by standing behind another person such that the camera cannot track the occluded person. Another camera that is facing a different direction (for example, being perpendicular to the first camera) may view the occluded person. Although FIG. 7A illustrates an example system with four cameras installed at 90-degree angles to one another, any number of cameras may be used and the cameras may be installed at any viewing angle relative to one another.

The cameras may be installed in a way which facilitates accurate coordinate transformations. For example, as shown in FIG. 7A, the Z axis, which may correlate to depth information, of camera1 7706 translates to the X axis of adjacent right angle camera4 7708. Furthermore, as shown in FIG. 7A, the X axis of camera1 7706 translates to the Z axis of camera2 7704 as follows:

Camera1: P1(x=2), P2(x=3), P3(x=4), P4(x=6).
Camera2: P1(z=2), P2(z=3), P3(z=4), P4(z=6).

Furthermore, the X axis of camera1 7706 translates to a reverse X axis of camera3 7702 as follows:

Camera1: P1(x=2), P2(x=3), P3(x=4), P4(x=6).
Camera3: P4(x=1), P3(x=3), P2(x=4), P1(x=5).

Figure 7B:
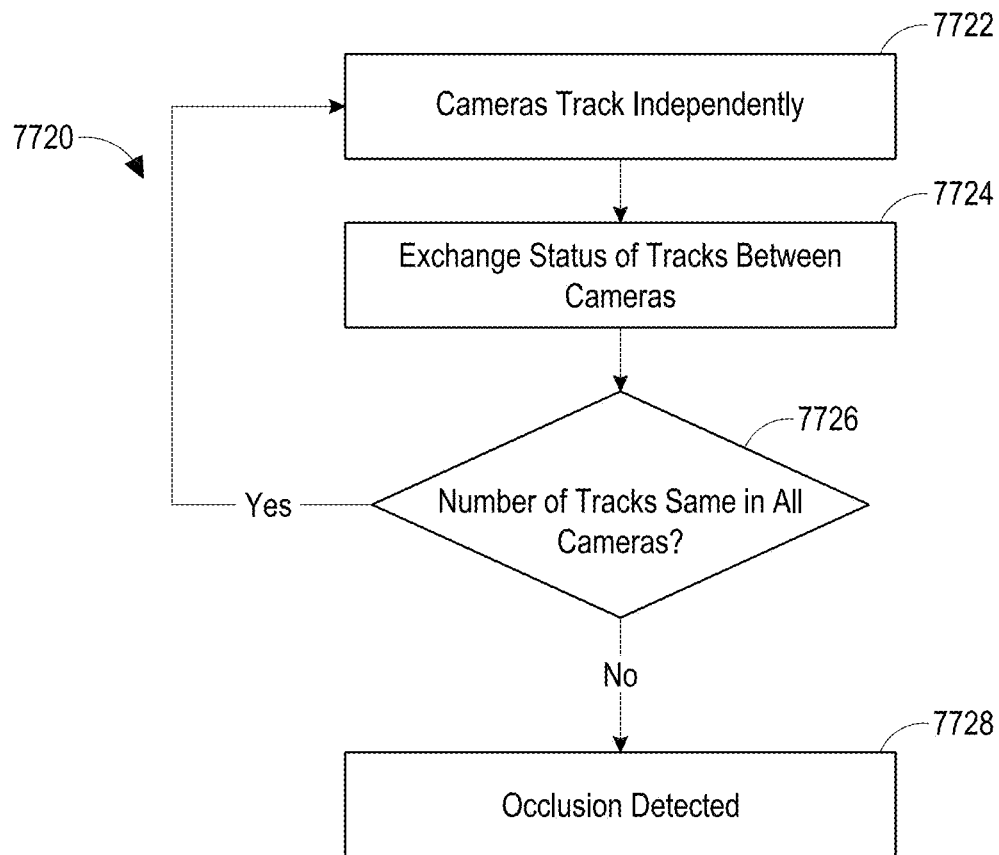
FIG. 7B illustrates an example process of detecting occlusions.

FIG. 7B illustrates an example process 7720 of detecting occlusions. At step 7722, the cameras track people independently. At step 7724, the cameras may exchange the status of tracks. The status of tracks may include number of tracked people, location of tracked people, identification of tracked people etc. At step 7726, if the number of tracked people is different between one or more cameras, then the processor of the imagers that has detected fewer number of tracked people may determine that an occlusion has been detected at step 7728. If at step 7726, the number of tracked people is the same among all the cameras, the processor of each imager determines that there is no occlusion occurring in those cameras.

In some example processes of detecting occlusions, the processors of the imagers may compare the status of tracks in one or more cameras with the number of people detected as having entered the room. If the status of tracks from an imager in which the number of tracks is the same as the entrance count, the processor of that imager can determine that there is no occlusion in the field of view of the associated camera. That processor can then send its status of trackers to a processor of another imager to determine if an occlusion is detected in the other imager. For example, as shown in FIG. 7A, if the processor associated with camera4 7708 determines that person P1 is occluded from the view of camera4 7708, the processor associated with camera1 7706 can transmit its status of trackers, including information relating to the tracking status of P1, to the processor associated with camera4 7708. Advantageously, the processors may be in communication with processors of other imagers of the system to transmit processed data with one another, without the need to transmit the data to a central point such as the server.

Additional examples of detection and/or tracking using cameras in a clinical setting are described in U.S. patent Ser. No. 10/007,758B2, the entirety of which is incorporated herein by reference and should form part of the disclosure.

Home & Additional Clinical Applications

In some implementations, any features of the clinical activity tracking system disclosed herein can be applied to a home setting. For example, a home activity tracking system can include one or more cameras in communication with a remote server, as described above. The home activity tracking system can be configured to detect whether a person has washed hands before and/or after handling food, before a meal, upon returning home from the outside, before handling an infant, and/or the like. The home activity tracking system can also improve home safety and/or security, for example but not limited to monitoring intruders, thefts, kitchen stove and/or a kettle left on, door(s) and/or window(s) left open, insects, snakes, fire, smoke, computer or screen time of a minor child, homework time of a minor child, people at home exhibiting illness, having an accident and/or sustaining injury, pet(s) activity, and/or the like.

As no images from the cameras are transferred to a central server, as described above, the home activity tracking system can improve privacy than when raw camera footage is saved. The information transmitted to the server can also be more secure from hacking, for example, due to only coordinates being sent to the server rather than an image of a person being tracked by the camera(s).

The home activity tracking features disclosed herein can also be incorporated into the clinical activity tracking system. The clinical activity tracking system can track moving objects in addition to tracking people as described above. For example, the clinical activity tracking system can track spiders, snakes, and/or the like for medical monitoring. A hospitalized patient may be immobilized or at least have greater difficulty moving the body or parts thereof compared to someone who is not hospitalized. The patient may be in bandages, connected to certain medical equipment, sedated, in a coma, or otherwise having difficulty to remove a moving object such as a crawling insect or snake, or even to alert the nurses or a caretaker. The clinical activity tracking system can be configured to recognize and detect certain moving objects (for example, within a certain distance and/or in contact with a patient's body and/or bed), and output an alarm to a remote server, which can alert the nurses or anyone else to help remove the moving objects from the patient and/or the patient's bed.

Terminology

Many other variations than those described herein will be apparent from this disclosure. For example, certain acts, events, or functions of any of the algorithms described herein can be performed in a different sequence, can be added, merged, or left out altogether (for example, not all described acts or events are necessary for the practice of the algorithms). Moreover, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular example of the examples disclosed herein. Thus, the examples disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the examples disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another example, a processor can include an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the examples disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various examples, it will be understood that various omissions, substitutions, and changes in the form and details of the devices or algorithms illustrated can be made without departing from the spirit of the disclosure. As will be recognized, the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A system for monitoring of hand hygiene compliance on a local network in a clinical room, the clinical room including a patient zone and a hand hygiene station outside the patient zone, the system comprising:
   a first camera configured to capture first image data from a first viewpoint in the clinical room;
   a first hardware processor configured to detect a person in an image frame from the first image data and assign a boundary box to the person, the first processor further configured to track movement of the boundary box in subsequent image frames from the first image data;
   a second camera configured to capture second image data from a second viewpoint in the clinical room;
   a second hardware processor configured to detect whether a hand hygiene activity has been performed from the second image data; and
   a plurality of display devices in different locations of the clinical room, the first processor and/or the second processor in communication with the plurality of the display devices,
   wherein the first and/or second processors are further configured to receive configuration information of the clinical room from a server upon initiation of the system, wherein the configuration information comprises one or more of display device locations, camera locations, an entrance location, a hand hygiene station location, and/or a patient bed location, and
   wherein the first and second processors are in communication with each other, the first or second processor further configured to:
      determine that the person to whom the boundary box is assigned has not performed the hand hygiene activity,
      locate, based at least in part on the configuration information, a nearest display device of the plurality of display devices to the person, wherein the person is entering the patient zone, and
      output an alert to the nearest display device.

2. The system of claim 1, wherein the first processor is configured to output the alert to the nearest display device.

3. The system of claim 1, wherein the first and second viewpoints are fixed.

4. The system of claim 1, wherein the first camera faces an entrance of the clinical room.

5. The system of claim 1, wherein the second camera faces the hand hygiene station in the clinical room.

6. The system of claim 5, wherein the second camera faces downward at the hand hygiene station.

7. The system of claim 5, wherein the second processor is configured to detect a handwashing activity or a hand sanitizing activity at the hand hygiene station.

8. The system of claim 1, comprising a third camera, wherein the third camera is configured to capture third image data from a third viewpoint in the clinical room.

9. The system of claim 1, wherein the first processor is configured to assign a contaminated status to any person upon first detection of said any person.

10. The system of claim 9, wherein the first or second processor is configured to change the contaminated status to a clean status upon detection of said any person having performed the hand hygiene activity.

11. The system of claim 1, wherein no image data from the first or second cameras is transmitted to the server or any of the plurality of display devices, or stored or recorded.

12. The system of claim 1, wherein the second processor is configured to detect the hand hygiene activity from the second image data by extracting hand hygiene-related features from image frames of the second image data.

13. The system of claim 1, wherein the second processor is configured to detect the hand hygiene activity from the second image data using deep learning modules.

14. A system for monitoring activities or actions occurring in a clinical setting comprising a hospital bed, the system comprising:
   a plurality of sensors including a first camera and a second camera in the clinical setting, the first and second cameras being high-resolution cameras, wherein the first and second cameras are facing a fixed object at different angles and relative positions of the first and second camera being fixed, the plurality of sensors further comprising at least one camera processor in electrical communication with the first and/or second cameras; and
   a plurality of display devices,
   wherein the at least one camera processor is in communication with a server, the at least one camera processor configured to process images captured by the first and/or second cameras to output data to the server and assign a boundary box to the person, the at least one camera processor further configured to track movement of the boundary box in subsequent image frames from the data, and
   wherein the server is configured to detect an event of hand hygiene incompliance by detecting the person to whom the boundary box is assigned having not performed a hand hygiene activity and assign a contaminated status to the person, the server further configured to output an alarm to one of the plurality of display devices in response to the person being within a predetermined distance from the hospital bed, wherein the one of the plurality of display devices is a display device nearest to the person or the hospital bed.

15. The system of claim 14, wherein the data comprises boundary box coordinates, tag identifier information, extracted facial features, activity features, camera identifier information, unique ID for each person, frame number of the images, or any combinations thereof.

16. The system of claim 15, wherein the first and/or second cameras are configured to prioritize detection of the unique ID for each person.

17. The system of claim 14, wherein the fixed object is the hospital bed and the first and second cameras are at opposite sides of the hospital bed.

18. The system of claim 14, wherein the plurality of sensors further comprises a third camera facing a hand hygiene station.

19. The system of claim 14, wherein the plurality of devices displays are displays of a plurality of patient monitoring systems.

20. The system of claim 14, wherein the plurality of sensors further comprises at least one microphone.

* * * * *